US010874839B2

(12) United States Patent
Matlock et al.

(10) Patent No.: US 10,874,839 B2
(45) Date of Patent: Dec. 29, 2020

(54) ADJUSTABLE INSTRUMENT FOR DILATION OF ANATOMICAL PASSAGEWAY

(71) Applicants: Acclarent, Inc., Irvine, CA (US); Biosense Webster (Israel) Ltd., Yokneam (IL)

(72) Inventors: George L. Matlock, Pleasanton, CA (US); Yehuda Algawi, Binyamina (IL); Ilya Sitnitsky, Nahariya (IL); Andres C. Altmann, Haifa (IL); Ygal Zucker, Haifa (IL); Don Q. Ngo-Chu, Irvine, CA (US); Vadim Gliner, Haifa (IL); Christopher T. Beeckler, Brea, CA (US); John H. Thinnes, Jr., Mission Viejo, CA (US); Assaf Govari, Haifa (IL)

(73) Assignees: Acclarent, Inc., Irvine, CA (US); Biosense Webster (Israel) Ltd., Yokneam (IL)

( * ) Notice: Subject to any disclaimer, the term of this patent is extended or adjusted under 35 U.S.C. 154(b) by 212 days.

(21) Appl. No.: 16/032,471

(22) Filed: Jul. 11, 2018

(65) Prior Publication Data

US 2019/0015645 A1    Jan. 17, 2019

Related U.S. Application Data

(60) Provisional application No. 62/531,977, filed on Jul. 13, 2017, provisional application No. 62/555,841, filed on Sep. 8, 2017.

(51) Int. Cl.
*A61M 29/02*     (2006.01)
*A61M 25/01*     (2006.01)
(Continued)

(52) U.S. Cl.
CPC ............... *A61M 29/02* (2013.01); *A61B 1/07* (2013.01); *A61B 1/233* (2013.01); *A61B 17/24* (2013.01);
(Continued)

(58) Field of Classification Search
CPC .................. A61M 29/00; A61M 29/02; A61M 2029/025; A61M 25/1011; A61M 25/10;
(Continued)

(56) References Cited

U.S. PATENT DOCUMENTS 4,551,292 A    11/1985   Fletcher et al.
7,720,521 B2    5/2010   Chang et al.
(Continued)

FOREIGN PATENT DOCUMENTS

CN    107233656 A    10/2017
EP    2018205 A1    1/2009
(Continued)

OTHER PUBLICATIONS

Merriam-Webster definition for "about" as accessed May 4, 2020; https://www.nnerriam-webster.com/dictionary/about.*
(Continued)

*Primary Examiner* — Wade Miles
(74) *Attorney, Agent, or Firm* — Frost Brown Todd LLC

(57) ABSTRACT

An apparatus includes a body, a shaft assembly, a deflection actuation assembly, and a dilation catheter. The shaft assembly includes a rigid proximal portion and a flexible distal portion. The deflection actuation assembly includes a rotary actuator and a first translatable actuation member at least partially disposed within the first rotary actuator. A second translatable actuation member extends through the shaft assembly and couples the first translatable actuation member with the flexible distal portion of the shaft assembly. The first rotary actuator is rotatable about a longitudinal axis to
(Continued)

thereby drive the first and second translatable actuation members longitudinally. The flexible distal portion is configured to deflect away from the longitudinal axis in response to translation of the first and second translatable actuation members longitudinally. The dilation catheter is slidable relative to the shaft assembly and includes an expandable dilator.

20 Claims, 21 Drawing Sheets

(51) Int. Cl.
*A61B 17/00* (2006.01)
*A61M 25/00* (2006.01)
*A61B 17/34* (2006.01)
*A61M 25/09* (2006.01)
*A61B 17/24* (2006.01)
*A61B 1/07* (2006.01)
*A61B 1/233* (2006.01)
*A61M 25/10* (2013.01)
*A61B 1/00* (2006.01)
*A61B 1/005* (2006.01)

(52) U.S. Cl.
CPC ..... *A61B 17/3421* (2013.01); *A61M 25/0113* (2013.01); *A61M 25/0136* (2013.01); *A61M 25/0147* (2013.01); *A61M 25/09* (2013.01); *A61M 25/09041* (2013.01); *A61B 1/0052* (2013.01); *A61B 1/00183* (2013.01); *A61B 2017/00309* (2013.01); *A61B 2017/00323* (2013.01); *A61B 2217/005* (2013.01); *A61M 25/0041* (2013.01); *A61M 25/10* (2013.01); *A61M 25/10188* (2013.11); *A61M 2025/09125* (2013.01); *A61M 2025/1093* (2013.01); *A61M 2029/025* (2013.01); *A61M 2210/0618* (2013.01); *A61M 2210/0681* (2013.01)

(58) Field of Classification Search
CPC ........ A61M 25/0147; A61M 2025/015; A61M 25/0136; A61F 2/958; A61F 2002/9583; A61F 2002/9586
See application file for complete search history.

(56) References Cited

U.S. PATENT DOCUMENTS

| | | | |
|---|---|---|---|
| 8,123,722 | B2 | 2/2012 | Chang et al. |
| 8,190,389 | B2 | 5/2012 | Kim et al. |
| 8,320,711 | B2 | 11/2012 | Altmann et al. |
| 8,702,626 | B1 | 4/2014 | Kim et al. |
| 9,095,646 | B2 | 8/2015 | Chow et al. |
| 9,127,786 | B1 | 9/2015 | Arratia |
| 9,155,492 | B2 | 10/2015 | Jenkins et al. |
| 9,167,961 | B2 | 10/2015 | Makower et al. |
| 9,198,736 | B2 | 12/2015 | Kim et al. |
| 9,962,530 | B2 | 5/2018 | Johnson et al. |
| 2007/0208252 | A1 | 9/2007 | Makower |
| 2008/0009829 | A1* | 1/2008 | Ta ................. A61F 2/915 604/509 |
| 2008/0183128 | A1 | 7/2008 | Morriss et al. |
| 2010/0030031 | A1 | 2/2010 | Goldfarb et al. |
| 2010/0274188 | A1 | 10/2010 | Chang et al. |
| 2011/0004057 | A1 | 1/2011 | Goldfarb et al. |
| 2011/0060214 | A1 | 3/2011 | Makower |
| 2012/0071857 | A1 | 3/2012 | Goldfarb et al. |
| 2012/0078096 | A1* | 3/2012 | Krolik ............. A61M 5/007 600/435 |
| 2013/0274715 | A1 | 10/2013 | Chan et al. |
| 2014/0200444 | A1 | 7/2014 | Kim et al. |
| 2014/0364725 | A1 | 12/2014 | Makower |
| 2015/0112134 | A1 | 4/2015 | Suehara et al. |
| 2015/0313732 | A1* | 11/2015 | Fulton, III ......... A61B 17/22 623/1.11 |
| 2016/0008083 | A1 | 1/2016 | Kesten et al. |
| 2016/0015250 | A1 | 1/2016 | Suehara et al. |
| 2016/0058985 | A1 | 3/2016 | Lam et al. |
| 2016/0310042 | A1 | 10/2016 | Kesten et al. |
| 2017/0056632 | A1 | 3/2017 | Jenkins et al. |
| 2017/0266413 | A1* | 9/2017 | Khuu ............... A61M 25/0147 |
| 2018/0085174 | A1 | 3/2018 | Radtke et al. |
| 2018/0303505 | A1 | 10/2018 | Algawi et al. |
| 2019/0015646 | A1 | 1/2019 | Matlock et al. |
| 2019/0038301 | A1 | 2/2019 | Algawi et al. |

FOREIGN PATENT DOCUMENTS

| | | |
|---|---|---|
| EP | 2397108 A2 | 12/2011 |
| EP | 2976025 B1 | 12/2016 |

OTHER PUBLICATIONS

U.S. Appl. No. 62/640,598, entitled "Fluid Fitting for Dialation Instrument," filed Mar. 9, 2018.
U.S. Appl. No. 15/852,530, entitled "Reusable Navigation Guidewire," filed Dec. 22, 2017.
U.S. Appl. No. 15/861,959, entitled "Navigation Guidewire with Interlocked Coils," filed Jan. 4, 2018.
U.S. Appl. No. 15/933,737, entitled "Apparatus to Secure Field Generating Device to Chair," filed Mar. 23, 2018.
U.S. Appl. No. 15/955,232, entitled "Deflectable Guide for Medical Instrument," filed Apr. 17, 2018.
U.S. Appl. No. 16/032,489, entitled "Adjustable Instruments for Dilation of Anatomical Passageway," filed Jul. 11, 2018.
Dictionary.com definition for "Dilator" as accessed Aug. 14, 2020; https://www.dictionary.com/browse/dilator?s=t.
International Search Report and Written Opinion dated Nov. 21, 2018 for International Application No. PCT/US2018/042021, 19 pages.

\* cited by examiner

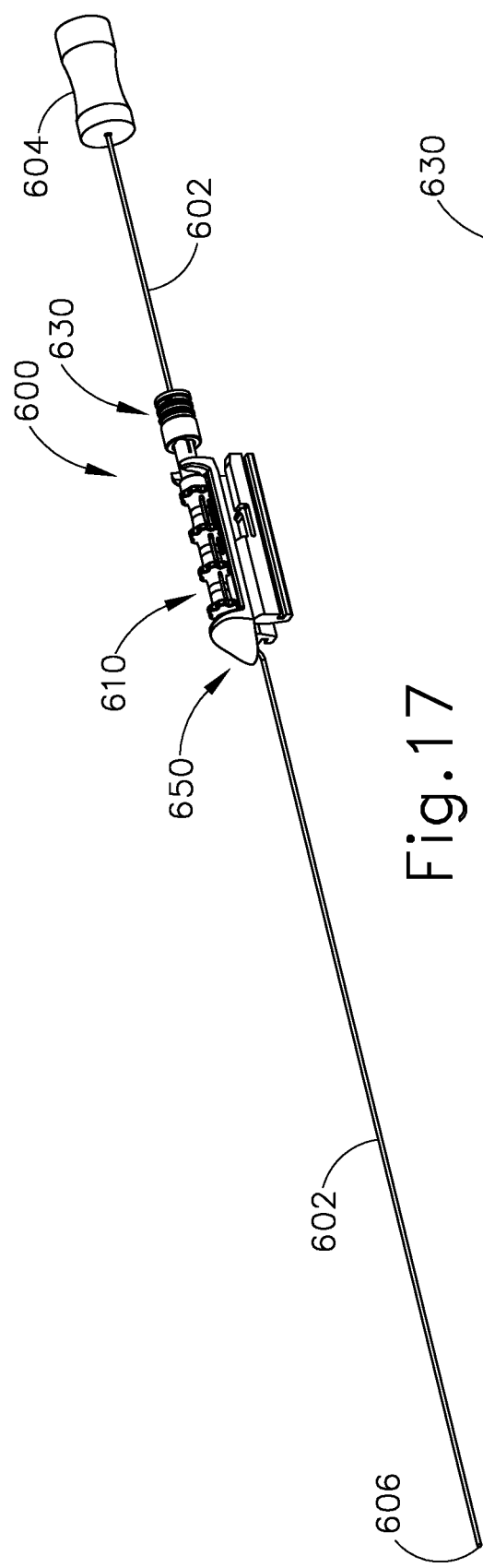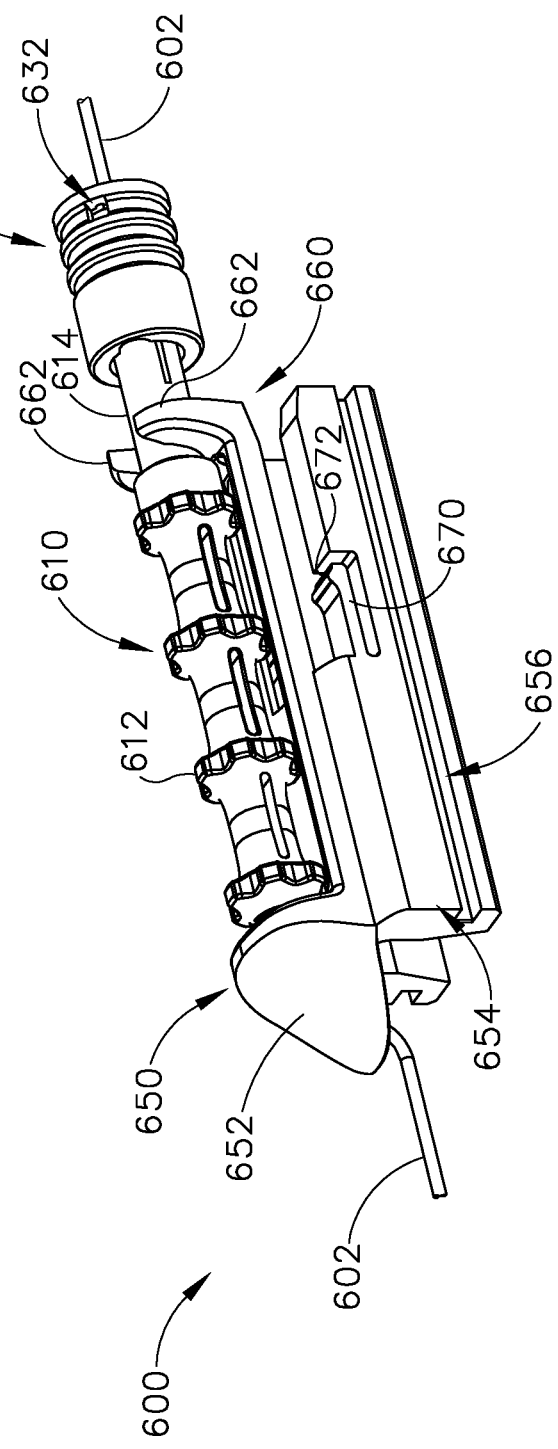

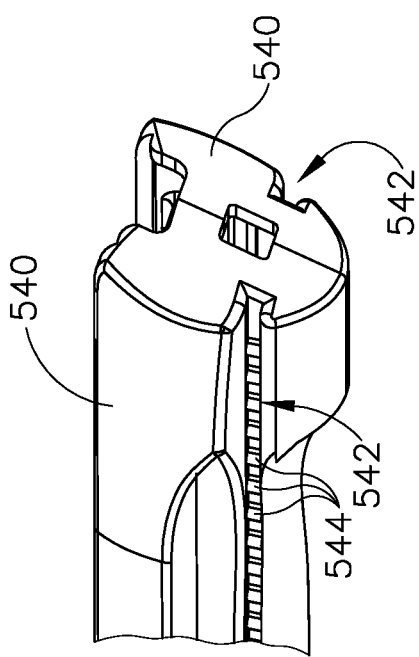
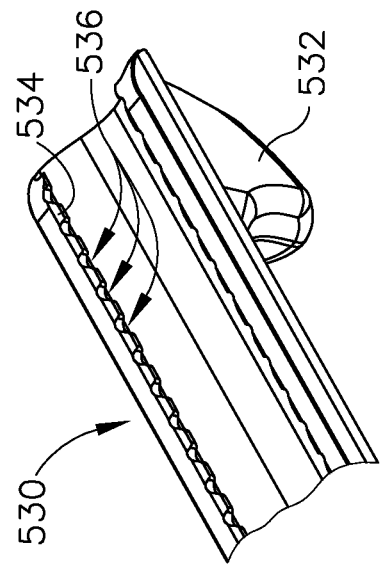
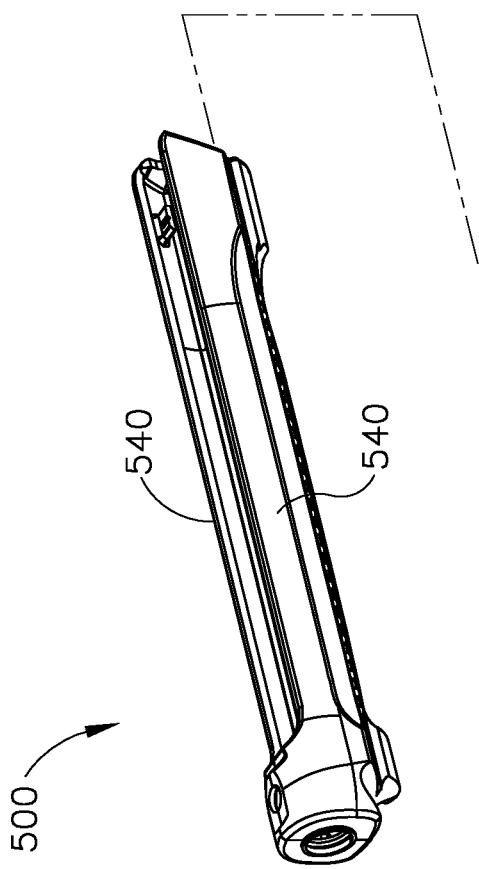
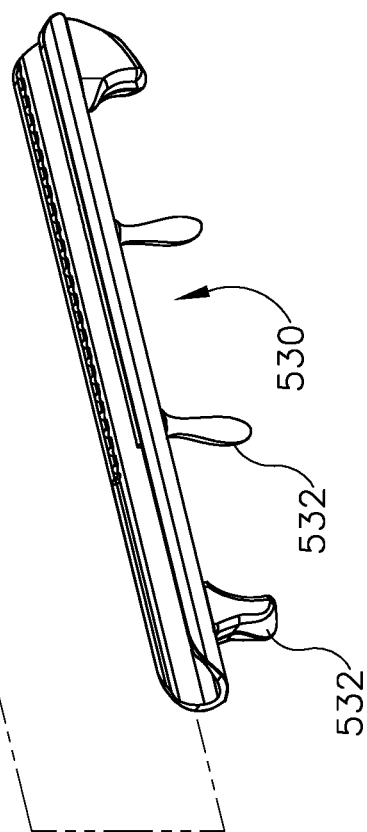

ADJUSTABLE INSTRUMENT FOR DILATION OF ANATOMICAL PASSAGEWAY

PRIORITY

This application claims priority to U.S. Provisional Pat. App. No. 62/531,977, entitled "Adjustable Instrument for Dilation of Anatomical Passageway," filed Jul. 13, 2017, the disclosure of which is incorporated by reference herein.

This application also claims priority to U.S. Provisional Pat. App. No. 62/555,841, entitled "Adjustable Instrument for Dilation of Anatomical Passageway," filed Sep. 8, 2017, the disclosure of which is incorporated by reference herein.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty System by Acclarent, Inc. of Irvine, Calif.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle ear and further provide improved drainage from the middle ear to the nasopharynx. Methods and devices for dilating the Eustachian tube are disclosed in U.S. Patent Pub. No. 2010/0274188, entitled "Method and System for Treating Target Tissue within the ET," published on Oct. 28, 2010, the disclosure of which is incorporated by reference herein; and U.S. Patent Pub. No. 2013/0274715, entitled "Method and System for Eustachian Tube Dilation," published on Oct. 17, 2013, the disclosure of which is incorporated by reference herein. An example of such a system is the Aera® Eustachian Tube Balloon Dilation System by Acclarent, Inc. of Irvine, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pat. No. 9,155,492, entitled "Sinus Illumination Lightwire Device," issued Oct. 13, 2015, the disclosure of which is incorporated by reference herein. An example of such an illuminating guidewire is the Relieva Luma Sentry® Sinus Illumination System by Acclarent, Inc. of Irvine, Calif.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation systems that may be used in IGS procedures is the CARTO® 3 System by Biosense-Webster, Inc., of Irvine, Calif. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

An example of an electromagnetic IGS systems that may be used in ENT and sinus surgery is the CARTO® 3 System by Biosense-Webster, Inc., of Irvine, Calif. When applied to functional endoscopic sinus surgery (FESS), balloon sinuplasty, and/or other ENT procedures, the use of IGS systems allows the surgeon to achieve more precise movement and positioning of the surgical instruments than can be achieved by viewing through an endoscope alone. As a result, IGS systems may be particularly useful during performance of FESS, balloon sinuplasty, and/or other ENT procedures where anatomical landmarks are not present or are difficult to visualize endoscopically. Examples of use of an IGS system in an ENT procedure are described in U.S. Pat. Pub. No. 2014/0364725, entitled "Systems and Methods for Performing Image Guided Procedures within the Ear, Nose, Throat and Paranasal Sinuses," published Dec. 11, 2014, the disclosure of which is incorporated by reference herein; and U.S. patent application Ser. No. 15/933,737, entitled "Apparatus to Secure Field Generating Device to Chair," filed Mar. 23, 2018, the disclosure of which is incorporated by reference herein.

It may be desirable to provide easily controlled placement of a balloon of a dilation catheter in an anatomical passageway, including in procedures that will be performed only by a single operator. While several systems and methods have been made and used to position a balloon of a dilation catheter in an anatomical passageway, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 17 depicts a perspective view of a guidewire actuation assembly of the instrument of FIG. 1A;

FIG. 18 depicts an enlarged perspective view of actuators of the guidewire actuation assembly of FIG. 17, with a collet collar in a proximal position;

FIG. 29 depicts a perspective view of handle components of the instrument of FIG. 1A, with a grip member separated from handle housings;

FIG. 30 depicts a partial perspective view of proximal portions of the handle housings of FIG. 29; and FIG. 31 depicts a partial perspective view of a proximal portion of the grip member of FIG. 29.

Figure 1A:
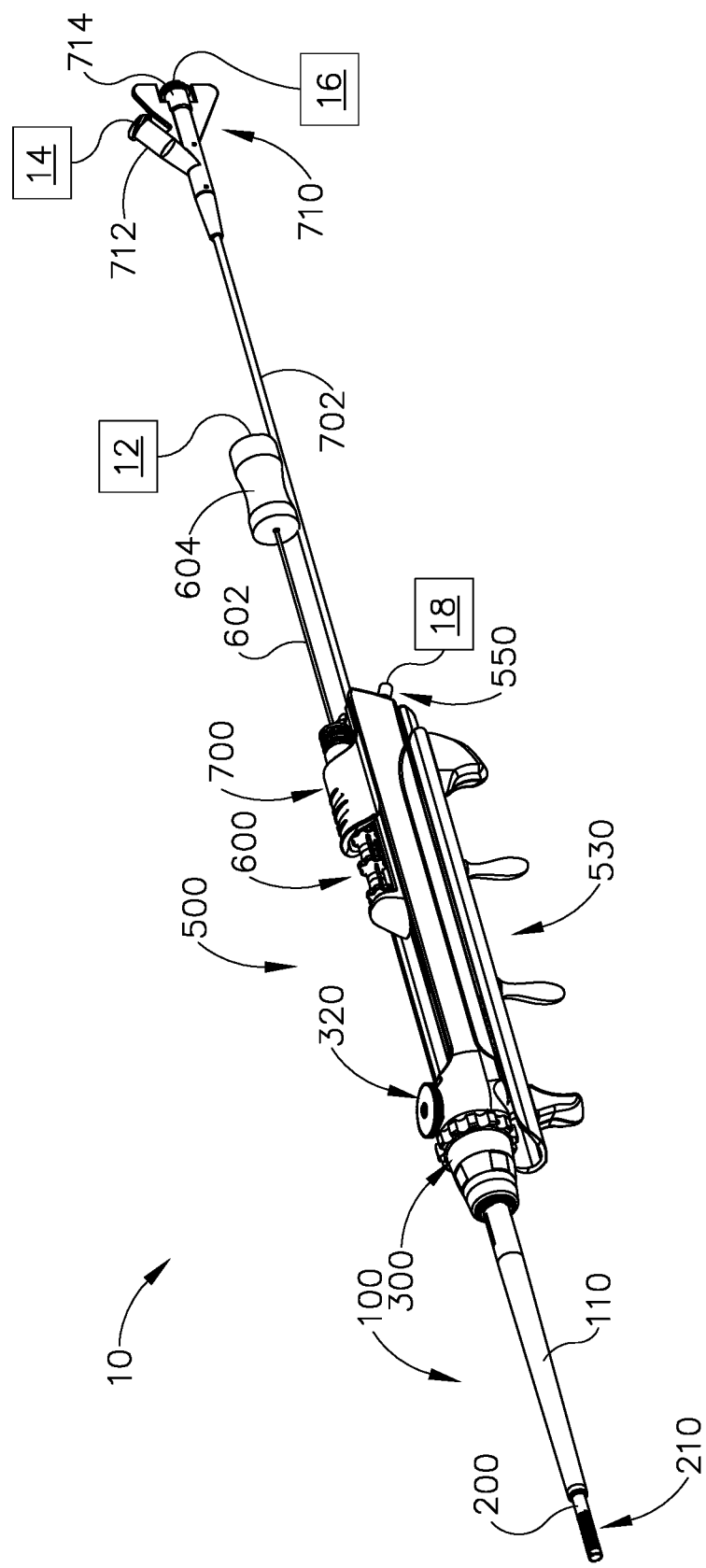
FIG. 1A depicts a perspective view of an exemplary dilation instrument, with a guidewire and a dilation catheter each in respective proximal positions.
Figure 1B:
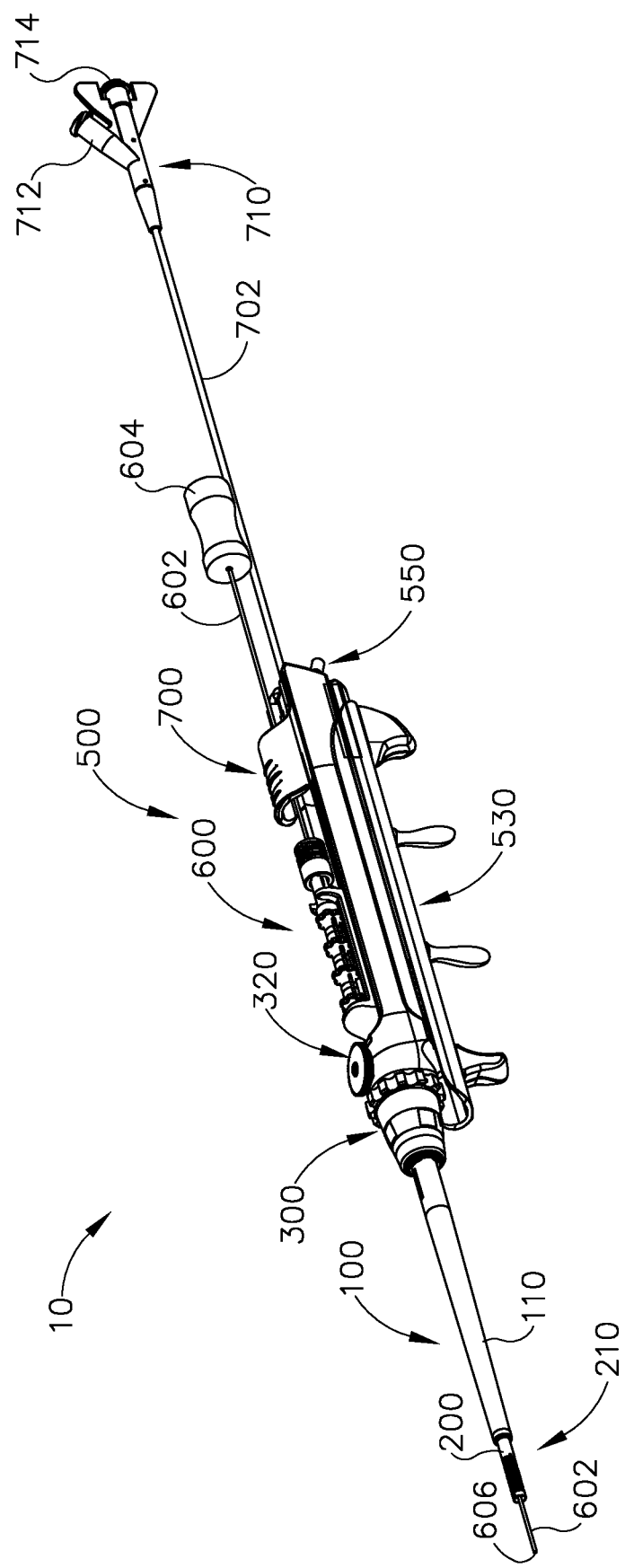
FIG. 1B depicts a perspective view of the instrument of FIG. 1A, with the guidewire in a distal position and the dilation catheter in the proximal position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Dilation Instrument

A. Overview

FIGS. 1A-1D show an exemplary dilation instrument (10) that may be used to dilate the ostium of a paranasal sinus, to dilate another passageway associated with drainage of a paranasal sinus, to dilate a Eustachian tube, or to dilate some other anatomical passageway (e.g., within the ear, nose, or throat, etc.). As will be described in greater detail below, dilation instrument (10) of the present example provides adjustability that enables the operator to use dilation instrument (10) in different scenarios, without requiring the operator to switch between different instruments. For instance, dilation instrument (10) may be used to dilate various different anatomical passageways (e.g., frontal sinus ostium, frontal recess, maxillary sinus ostium, sphenoid sinus ostium, ethmoid sinus ostium, Eustachian tube, etc.) by making simple adjustments to structural features of the instrument.

Dilation instrument (10) of this example includes a handle assembly (500), a guide shaft assembly (100) extending distally from handle assembly (500); a guidewire actuation assembly (600) slidably coupled with handle assembly (500); and a dilation catheter actuation assembly (700) slidably coupled with handle assembly (500). A guidewire module (12) is coupled with a guidewire (602) of dilation instrument (10) via a connector (604). An inflation fluid source (14) and an irrigation fluid source (16) are coupled with a dilation catheter (702) of dilation instrument (10) via a connector (710). A suction source (18) is coupled with a suction conduit (802) (FIG. 14) of dilation instrument (10) via a suction port (550).

Handle assembly (500) is sized and configured to be grasped and operated by a single hand of an operator. The operator may selectively operate guidewire actuation assembly (600) and dilation catheter actuation assembly (700) with the same single hand that grasps handle assembly (500). As shown in the transition from FIG. 1A to FIG. 1B, the operator may advance guidewire actuation assembly (600) distally along handle assembly (500) to thereby advance guidewire (602) distally, such that the distal end (606) of guidewire (602) is positioned distal to the distal end of guide shaft assembly (100). As shown in the transition from FIG. 1B to FIG. 1C, the operator may advance dilation catheter actuation assembly (700) distally along handle assembly (500) to thereby advance dilation catheter (702) distally, such that the distal tip (720) of dilation catheter (702) is positioned distal to the distal end of guide shaft assembly (100). With dilation catheter (702) advanced to a distal position, the operator may then inflate a dilator (722) of dilation catheter (702) to achieve an expanded state as shown in FIG. 1D, to thereby dilate an anatomical passageway in which dilator (722) is positioned.

In the present example, dilation catheter (702) is coaxially disposed within guide shaft assembly (100), and guidewire (602) is coaxially disposed within dilation catheter (702). In some other versions, guide shaft assembly (100) is coaxially disposed within dilation catheter (702), and guidewire (602) is coaxially disposed within guide shaft assembly (100). Also in some versions, guidewire (602) is omitted.

Examples of features and functionalities of the above-noted components of dilation instrument (10) are described in greater detail below. These features and functionalities are merely illustrative examples. By way of further example only, the features and functionalities described herein may be modified in accordance with the teachings of U.S. Pat. App. Ser. No. 16/032,489, entitled "Adjustable Instrument for Dilation of Anatomical Passageway," filed on even date herewith, the disclosure of which is incorporated by reference herein. Other variations of the features and functionalities described herein will be apparent to those skilled in the art in view of the teachings herein.

B. Exemplary Guide Shaft Assembly and Associated Actuation Assemblies

FIGS. 2-16 show various components of guide shaft assembly (100) in greater detail. Guide shaft assembly (100) of this example includes a rigid shaft member (110), a flexible shaft member (200), a push-pull wire (230), a cam barrel (130), and a deflection control knob (300). Shaft members (110, 200), cam barrel (130), and deflection control knob (300) are coaxially aligned with each other in this example, with push-pull wire (230) being laterally offset from the central longitudinal axis shared by shaft members (110, 200), cam barrel (130), and deflection control knob (300). As will be described in greater detail below, guide shaft assembly (100) is operable to guide guidewire (602) and dilation catheter (702) along an operator-selected exit angle relative to the central longitudinal axis of guide shaft assembly (100).

Figure 3A:
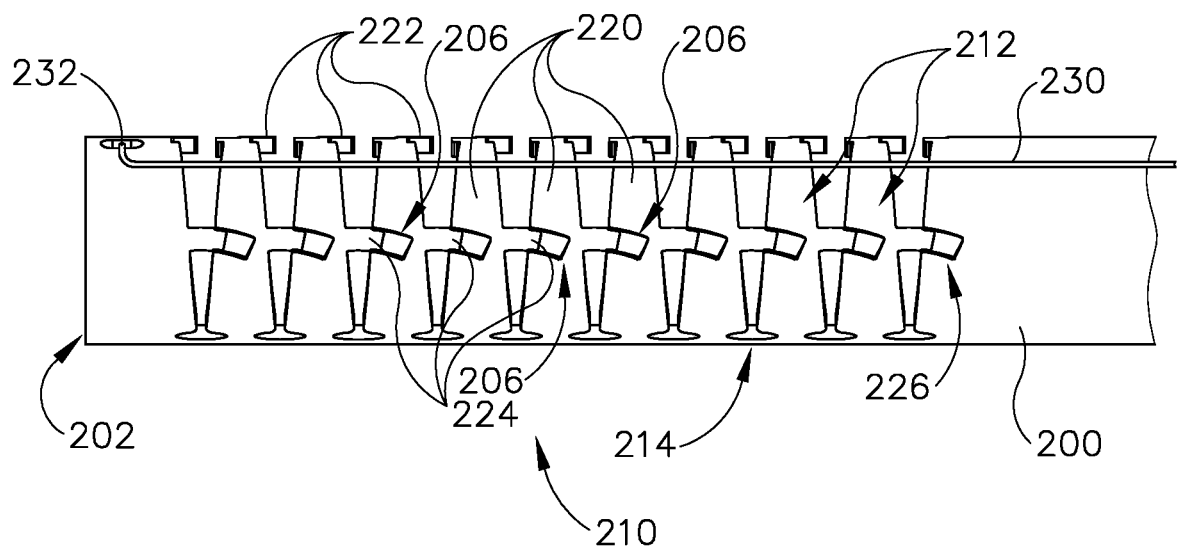
FIG. 3A depicts a cross-sectional side view of a distal portion of a flexible shaft member of the guide shaft assembly of FIG. 2, with the distal portion in a straight configuration.
Figure 3B:
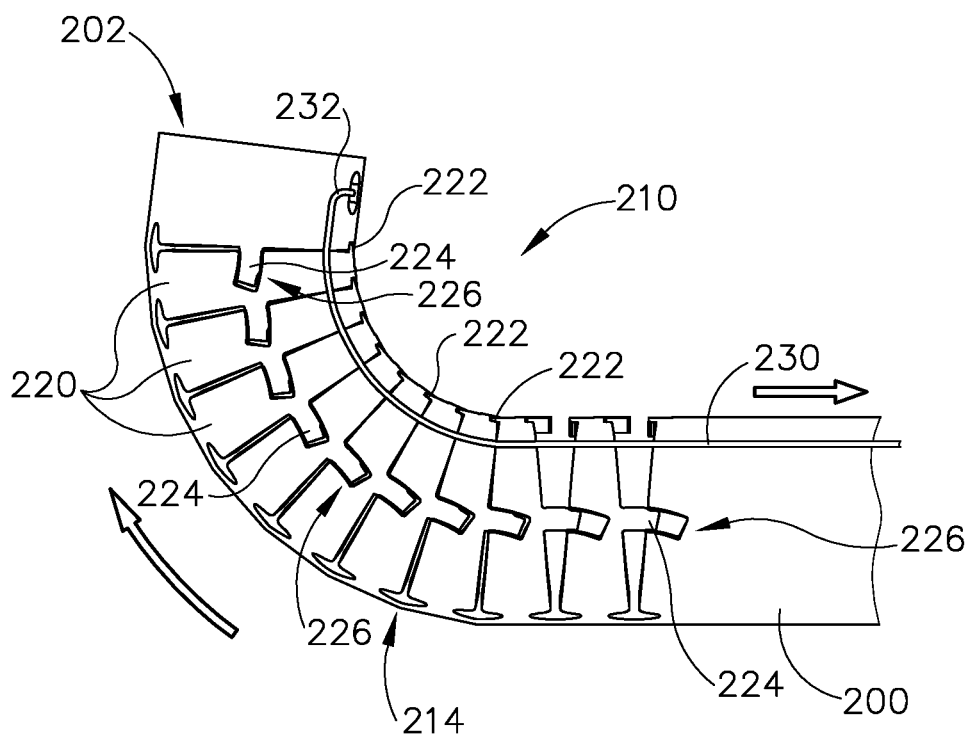
FIG. 3B depicts a cross-sectional side view of the flexible shaft member of FIG. 3A in a bent configuration.

In some versions, both shaft members (110, 200) are formed of a metallic material, such as stainless steel and/or nitinol. In some such versions, shaft members (110, 200) (and at least some other portions of instrument (10)) may be reusable, with such reusable components being subject to cleaning and sterilization between uses on different patients. In some other versions, one or both of shaft members (110, 200) may be formed of a polymeric material. In some such versions, shaft members (110, 200) may be treated as single-use-only components. Flexible shaft member (200) is secured to rigid shaft member (110) and is positioned distally in relation to rigid shaft member (110). As best seen in FIGS. 3A-3B, flexible shaft member (200) includes a flex section (210) that is formed by a series of ribs (220), which are separated by a series of notches (212). Notches (212) are generally V-shaped, with a circular opening at the vertex of each "V." Notches (212) also include tab portions (224) that fit in corresponding sub-notches (226). The top of each "V" includes a set of stop features (222).

As shown in FIG. 3A, when flex section (210) is in a straight configuration, tab portions (224) are disposed in corresponding sub-notches (226) but are not fully seated in sub-notches (226). As also shown in FIG. 3A, when flex section (210) is in a straight configuration, stop features (222) are separated from each other. FIG. 3B shows flex section (210) in a fully bent configuration. In this state, tab portions (224) are fully seated in sub-notches (226) and stop features (222) are engaged with each other. During the transition between the states shown in FIGS. 3A-3B, tab portions (224) and sub-notches (226) may cooperate to ensure that flex section (210) bends in a consistent fashion, with sufficient lateral stability; and that flex section (210) provides a consistent and stable bent or straight state.

By way of example only, flex section (210) may be formed through laser cutting or any other suitable manufacturing process. In some versions, flex section (210) is covered with a flexible wrap (not shown). Such a flexible wrap may prevent tissue and other structures from getting snagged or pinched in notches (212), without compromising the flexibility of flex section (210). A flexible wrap may also ensure that suction provided through guide shaft assembly (100) is focused at distal end (202). Various suitable forms that flex section (210) may take will be apparent to those of ordinary skill in the art in view of the teachings herein. By way of further example only, flex section (210) may be constructed and operable in accordance with at least some of the teachings of U.S. patent application Ser. No. 15/955,232, entitled "Deflectable Guide for Medical Instrument," filed Apr. 17, 2018, the disclosure of which is incorporated by reference herein.

Figure 11:
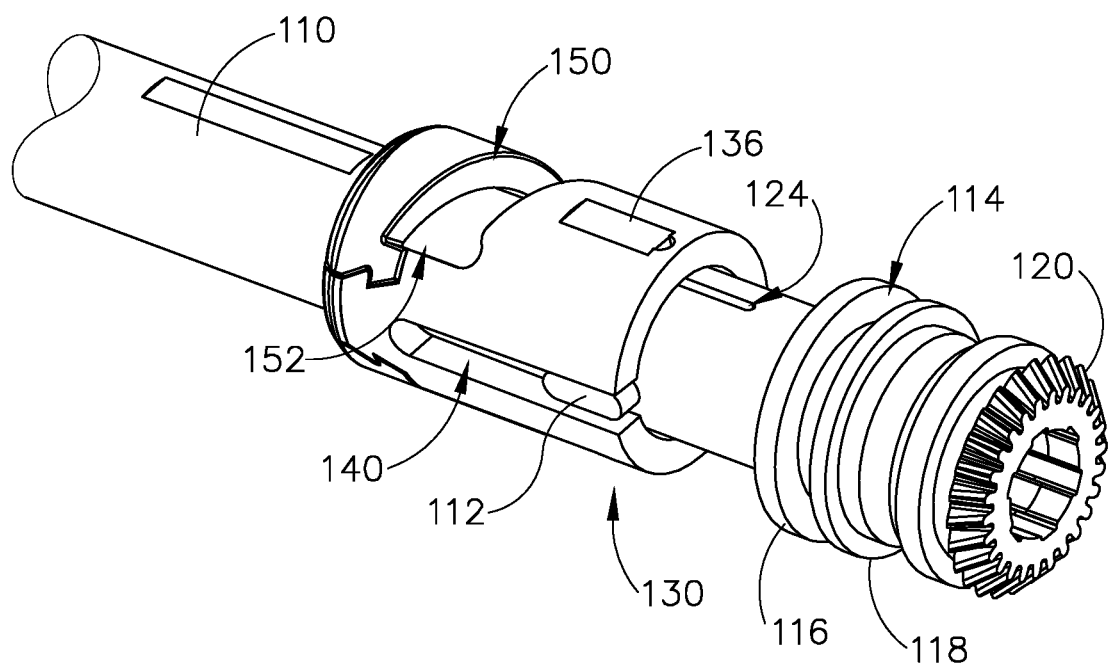
FIG. 11 depicts a perspective view of the cam barrel of FIG. 4 disposed about a proximal portion of the rigid shaft member of FIG. 10.

Push-pull wire (230) is disposed within shaft members (110, 200) and is operable to provide controlled bending of flex section (210). As shown in FIGS. 3A-3B, a distal end (232) of push-pull wire (230) is secured to the distal end (202) of flexible shaft member (200), distal to flex section (210). Push-pull wire (230) is disposed near the tops of the "V"s of notches (212). Thus, when push-pull wire (230) is pulled proximally, flex section (210) will bend to a deflected configuration. When push-pull wire (230) is pushed distally, flex section (210) will bend toward a straight configuration. A proximal end (234) of push-pull wire (230) (FIG. 2) is secured to a cam barrel (130) by a retention key (136) (FIG. 11). Proximal end (234) is threaded into one or more lateral openings (134) in a key recess (132) of cam barrel (130); and then key (136) is inserted into key recess (132) to retain proximal end (234) in openings (134). As will be described in greater detail below, translation of cam barrel (130) will cause translation of push-pull wire (230), which will thereby cause straightening or bending of flex section (210).

Figure 4:
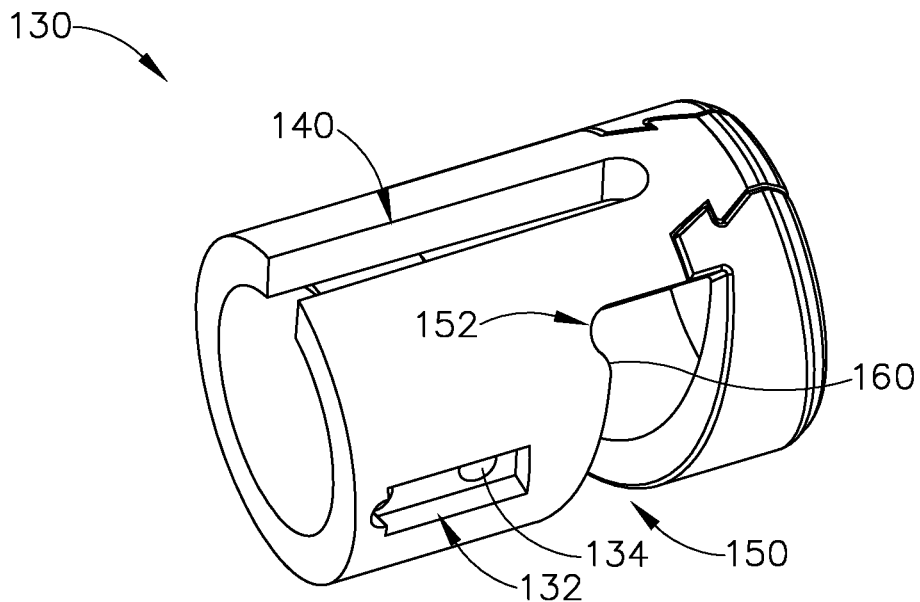
FIG. 4 depicts a perspective view of a cam barrel of the guide shaft assembly of FIG. 2.
Figure 5:
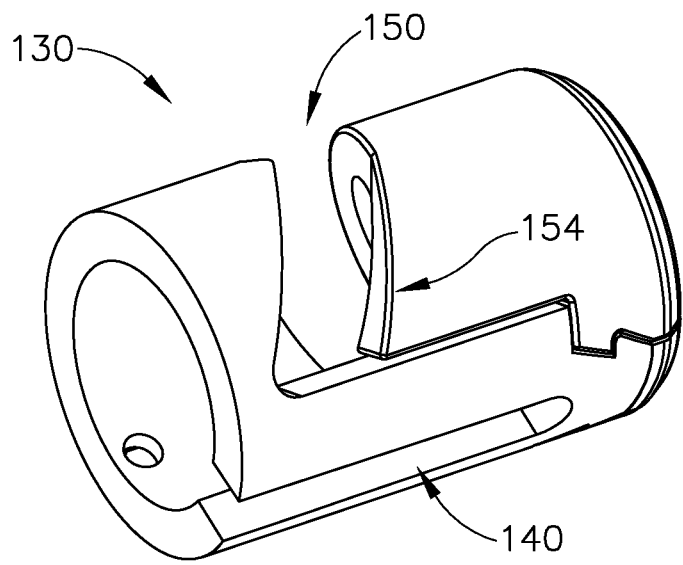
FIG. 5 depicts another perspective view of the cam barrel of FIG. 4.
Figure 6:
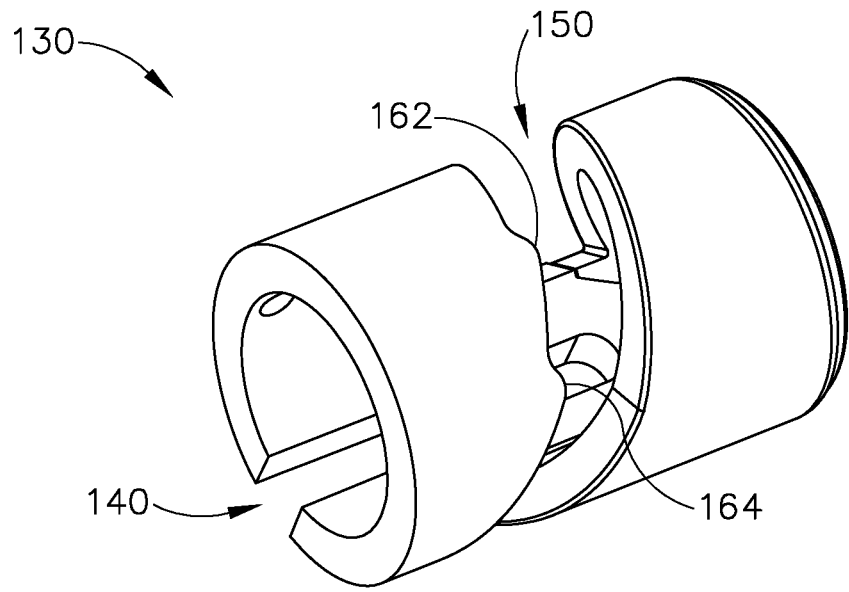
FIG. 6 depicts another perspective view of the cam barrel of FIG. 4.
Figure 7:
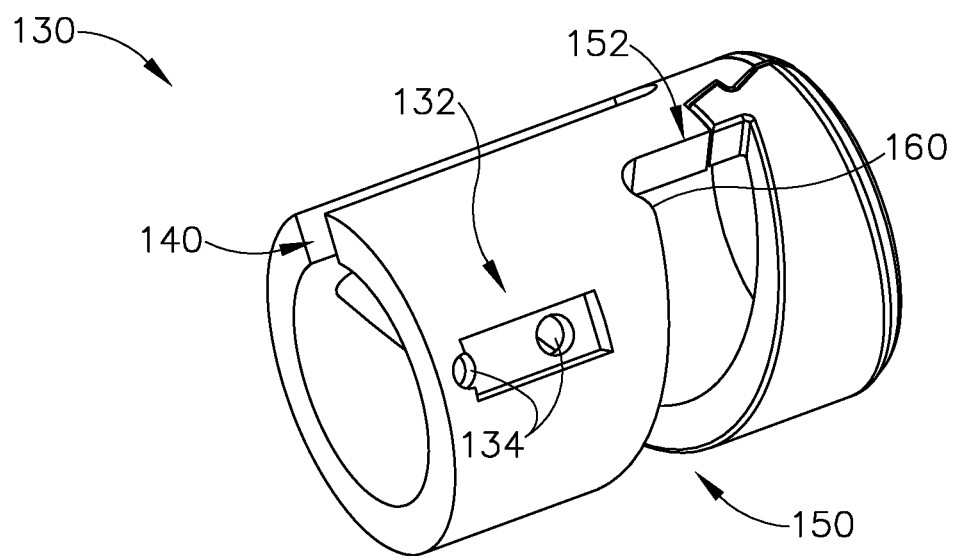
FIG. 7 depicts another perspective view of the cam barrel of FIG. 4.

As shown in FIGS. 4-7, cam barrel (130) includes a lateral channel (140) and a generally helical cam slot (150). Lateral channel (140) extends longitudinally from a proximal end of cam barrel (130) to a point that is proximal to the distal end of cam barrel (130). Thus, lateral channel (140) proximally opens at the proximal end of cam barrel (130); but distally terminates at a position proximal to the distal end of cam barrel (130). Cam slot (150) extends along a generally helical path, with features providing slight deviation from purely helical configurations, terminating at longitudinal points that are located between the distal and proximal ends of cam barrel (130). As best seen in FIGS. 4 and 7, a proximal end (152) of cam slot (150) includes a detent feature (160). As best seen in FIG. 6, an intermediate portion of cam slot (150) includes two detent features (162, 164). As best seen in FIG. 5, a distal end (154) of clam slot (150) does not include any detent features, though in some variations distal end (154) may include a detent feature if desired. When a tab (308) of deflection control knob (300) encounters detent features (160, 162, 164) as described in greater detail below, detent features (160, 162, 164) may provide slight resistance to further motion of tab (308), thereby providing tactile feedback to the operator and helping to maintain the position of tab (308) in cam slot (150). Cam slot (150) may have any suitable number of detent features (160, 162, 164), including more or fewer than three.

Cam barrel (130) is coupled with rigid shaft member (110) such that cam barrel (130) is allowed to slide longitudinally along rigid shaft member (110); yet cam barrel (130) is prevented from rotating about rigid shaft member (110). As shown in FIGS. 10-12B a tab (112) projects laterally and unitarily from a proximal portion of rigid shaft member (110); and is slidably disposed in lateral channel (140) of cam barrel (130). The fit between tab (112) and lateral channel (140) allows cam barrel (130) to slide longitudinally along rigid shaft member (110) while preventing cam barrel (130) from rotating about rigid shaft member (110). Other suitable structures may be used to achieve this relationship between rigid shaft member (110) and cam barrel (130).

Figure 2:
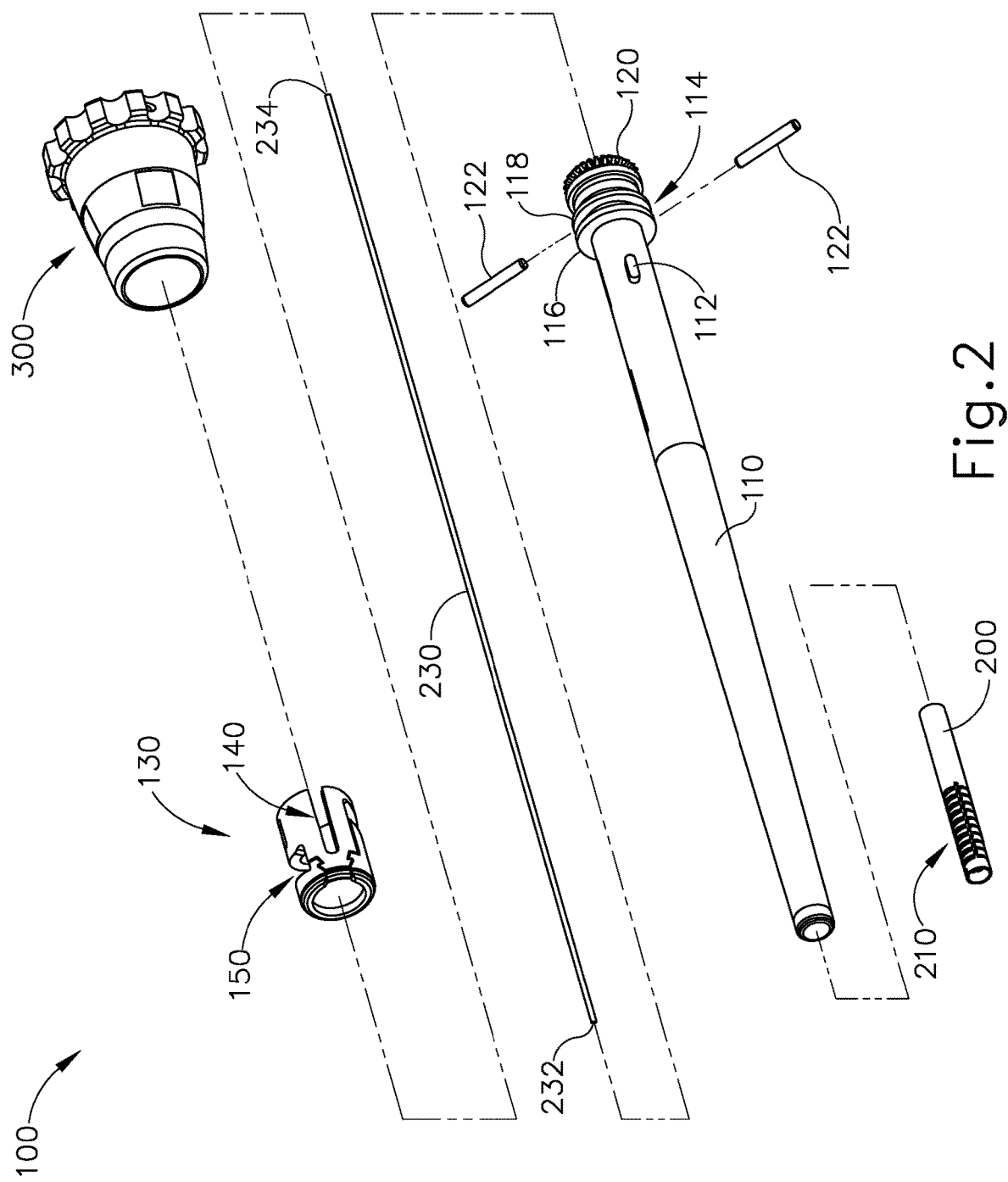
FIG. 2 depicts an exploded perspective view of a guide shaft assembly of the instrument of FIG. 1A.
Figure 13:
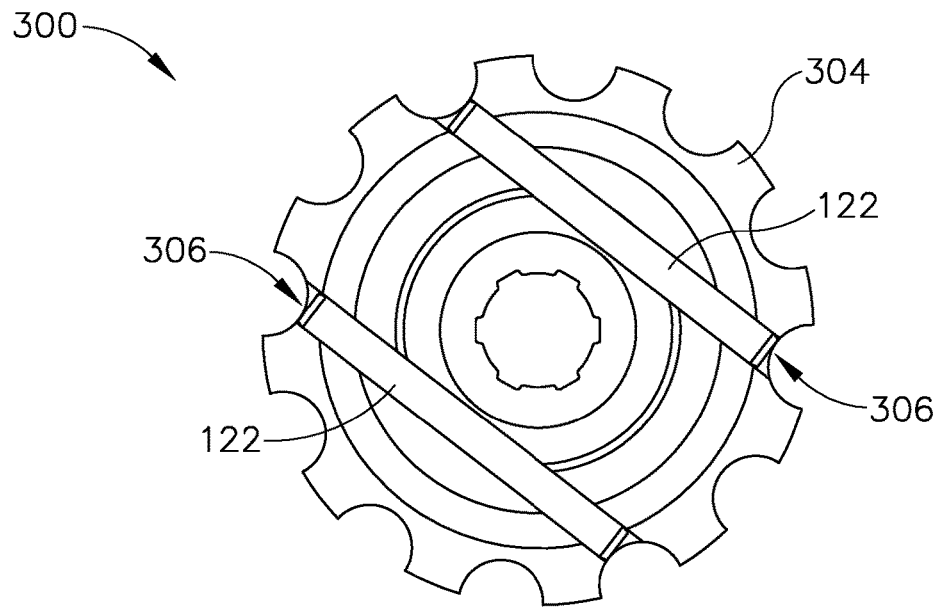
FIG. 13 depicts a cross-sectional end view of the deflection control knob of FIG. 8, with the cross-section taken at a position where retention pins are disposed in the deflection control knob.

As shown in FIG. 13, a pair of pins (122) are fixedly secured in corresponding openings (306) of deflection control knob (300). As shown in FIG. 2, pins (122) are captured in an annular space (114) defined between annular flanges (116, 118) at a proximal portion of rigid shaft member (110). The relationship between pins (122) and flanges (116, 118) allows deflection control knob (300) to rotate relative to rigid shaft member (110) while preventing deflection control knob (300) from translating relative to rigid shaft member (110). Other suitable structures may be used to achieve this relationship between rigid shaft member (110) and deflection control knob (300). The proximal end of deflection control knob (300) further includes gripping features (304) that are configured to promote an operator's grip of deflection control knob (300), thereby facilitating rotation of deflection control knob (300) relative to rigid shaft member (110).

Figure 9:
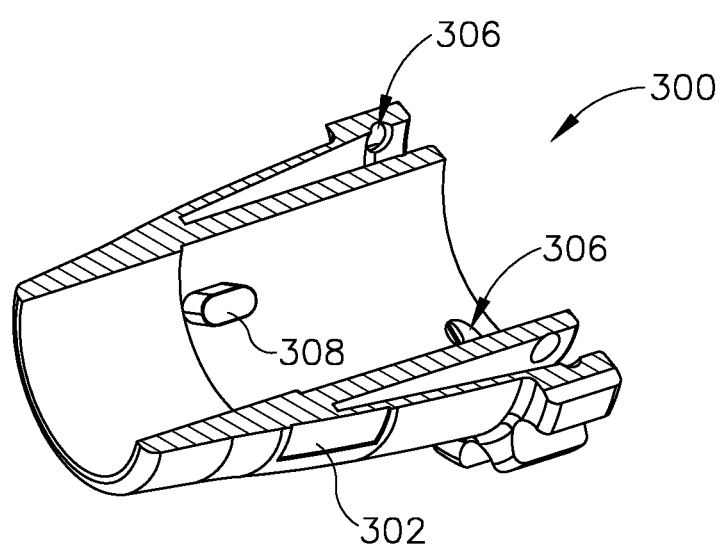
FIG. 9 depicts a cross-sectional perspective view of the deflection control knob of FIG. 8.
Figure 12A:
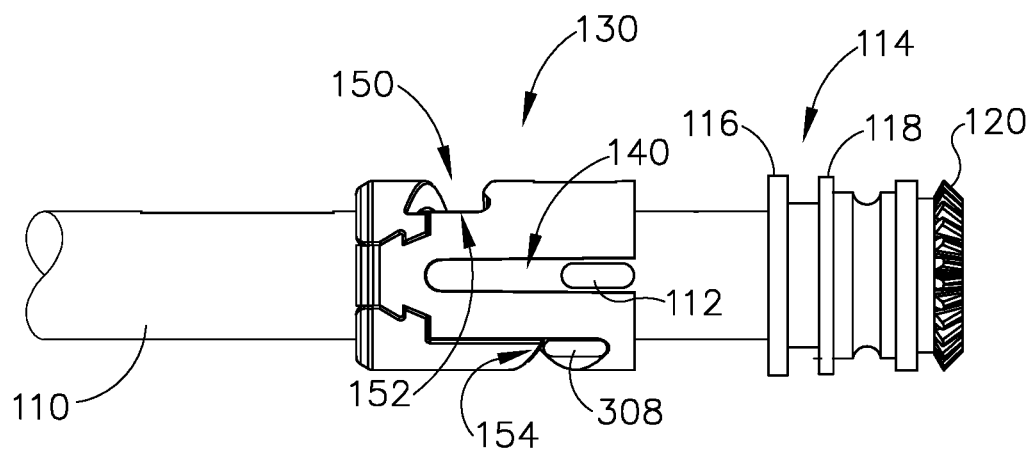
FIG. 12A depicts a plan view of the cam barrel of FIG. 4 disposed about a proximal portion of the rigid shaft member of FIG. 10, with the cam barrel in a distal position.
Figure 12B:
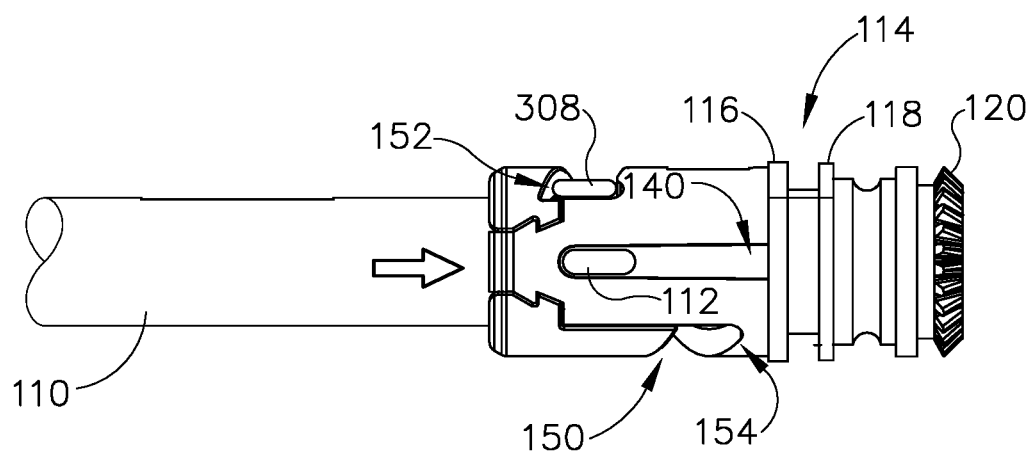
FIG. 12B depicts a plan view of the cam barrel of FIG. 4 disposed about a proximal portion of the rigid shaft member of FIG. 10, with the cam barrel in a proximal position.

As shown in FIG. 9, a tab (308) projects inwardly and unitarily in an interior region of deflection control knob (300). As shown (schematically) in FIGS. 12A-12B, tab (308) is configured and positioned to fit in cam slot (150) of cam barrel (130). Tab (308) is configured to slide along cam slot (150), between proximal end (154) (FIG. 12A) and distal end (152) (FIG. 12B). With tab (112) and lateral channel (140) cooperating to prevent cam barrel (130) from rotating relative to rigid shaft member (110), movement of tab (308) along cam slot (150) causes cam barrel (130) to translate longitudinally along rigid shaft member (110). Thus, when tab (308) is at proximal end (154) of cam slot (150) as shown in FIG. 12A, cam barrel (130) is at a distal position along rigid shaft member (110). When tab (308) is at distal end (152) of cam slot (150) as shown in FIG. 12B, cam barrel (130) is at a proximal position along rigid shaft member (110). Tab (308) traverses cam slot (150) when deflection control knob (300) is rotated relative to rigid shaft member (110).

Figure 10:
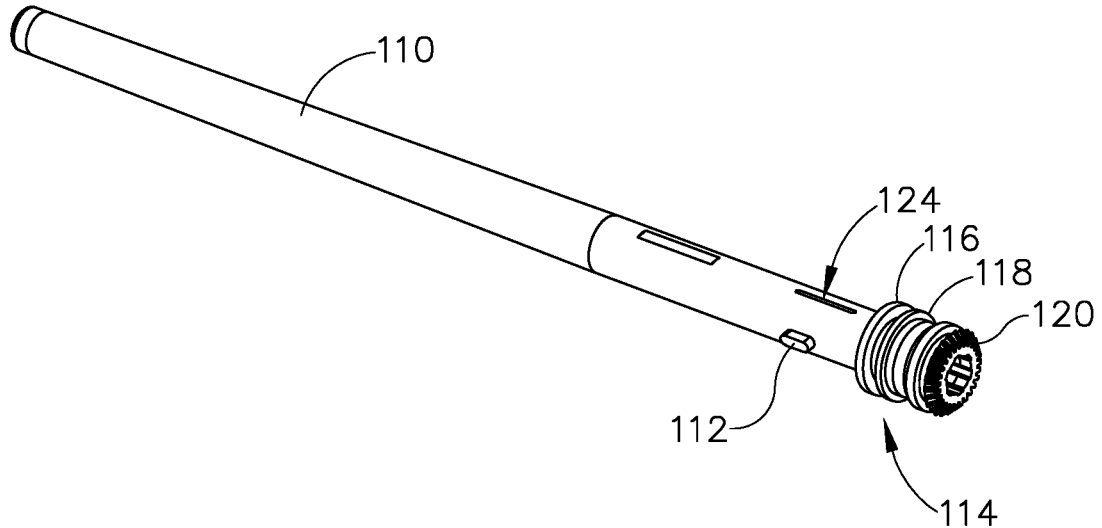
FIG. 10 depicts a perspective view of a rigid shaft member of the guide shaft assembly of FIG. 2.

As noted above, proximal end (234) of push-pull wire (230) is secured to cam barrel (130), such that push-pull wire (230) translates with cam barrel (130) relative to rigid shaft member (110) in response to rotation of deflection control knob (300) relative to rigid shaft member (110). As shown in FIGS. 10-12 one side of the proximal portion of rigid shaft member (110) includes an elongate slot (124). Slot (124) is configured to enable push-pull wire (230) to pass transversely through rigid shaft member (110) and translate relative to rigid shaft member (110). As also noted above, translation of push-pull wire (230) relative to rigid shaft member (110) causes lateral deflection of flex section (210). The operator may thus selectively deflect flex section (210) by rotating deflection control knob (300) relative to rigid shaft member (110).

Tab (308) encounters detents (160, 162, 164) as tab (308) traverses cam slot (150). These encounters may provide tactile feedback to the operator and may provide slight resistance to further rotation of deflection control knob (300). Detents (160, 162, 164) may be located at positions corresponding with predetermined deflection angles of flex section (210). When tab (308) is at proximal end (154) of cam slot (150) as shown in FIG. 12A, such that flex section (210) is in a straight configuration, shaft assembly (100) may be configured to easily guide guidewire (260) and dilation catheter (400) into a first anatomical passageway such as the sphenoid sinus ostium.

When deflection control knob (300) is rotated to a point where tab (308) reaches detent (164), flex section (210) may be in a first bent configuration defining a bend angle selected to facilitate access to a second anatomical passageway, such as the Eustachian tube. By way of example only, this bend angle may be from approximately 50 degrees to approximately 60 degrees, or more particularly at approximately 55 degrees. When deflection control knob (300) is further rotated to a point where tab (308) reaches detent (162), flex section (210) may be in a second bent configuration defining a bend angle selected to facilitate access to a third anatomical passageway, such as the frontal recess or frontal sinus ostium. By way of example only, this bend angle may be from approximately 65 degrees to approximately 70 degrees, or more particularly at approximately 70 degrees. When deflection control knob (300) is further rotated to a point where tab (308) reaches detent (160) at distal end (152), flex section (210) may be in a third bent configuration defining a bend angle selected to facilitate access to a fourth anatomical passageway, such as the maxillary sinus ostium. By way of example only, this bend angle may be from approximately 105 degrees to approximately 115 degrees, or more particularly at approximately 110 degrees.

Figure 8:
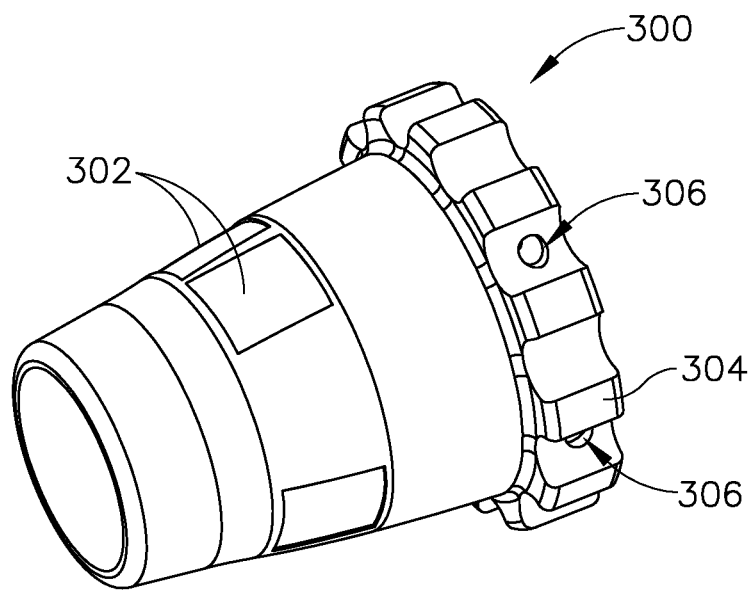
FIG. 8 depicts a perspective view of a deflection control knob of the guide shaft assembly of FIG. 2.

Once the operator achieves a desired angle of deflection of flex section (210), tab (308) and cam slot (150) may provide self-locking functionality such that flex section (210) may maintain the selected angle of deflection during subsequent normal use of instrument (10), until the operator again rotates deflection control knob (300) relative to rigid shaft member (110) to further adjust the angle of deflection. Since guidewire (602) and dilation catheter (702) are slidably positioned within shaft assembly (100), guidewire (602) and dilation catheter (702) will exit the distal end of shaft assembly (100) at whatever deflection angle the operator has selected. In view of the foregoing, an operator may readily achieve various exit angles for guidewire (602) and dilation catheter (702) by rotating deflection control knob (300) relative to rigid shaft member (110). The operator may thus readily dilate various anatomical passageways without having to exchange instruments; and without having to replace pieces of instrument (10). As shown in FIG. 8, deflection control knob (300) also includes markings (302) at various angular positions. These markings (302) may be observed to provide visual feedback indicating the deflection angle of flex section (210), supplementing the tactile feedback provided by detents (160, 162, 164).

Figure 14:
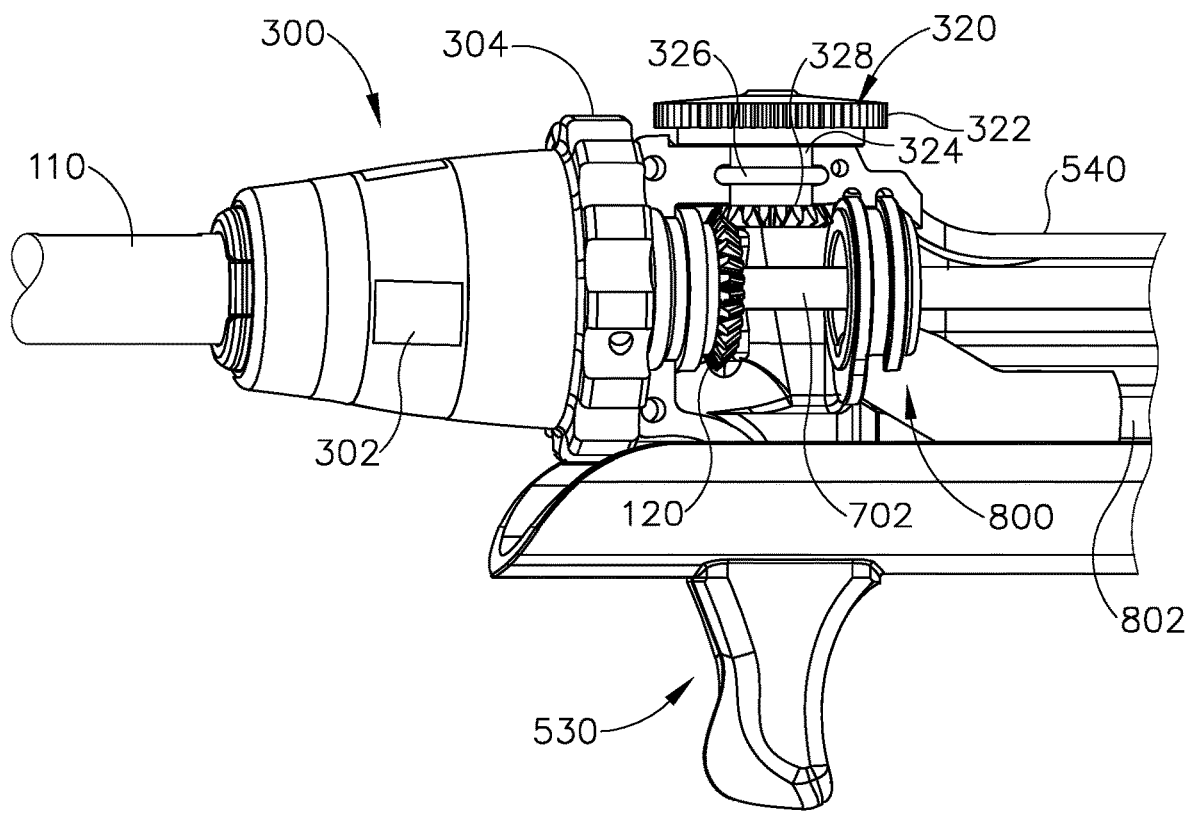
FIG. 14 depicts a side elevational view of a portion of the instrument of FIG. 1A, with a housing portion removed from a handle assembly of the instrument to reveal shaft rotation control components at the distal end of the handle assembly.
Figure 15:
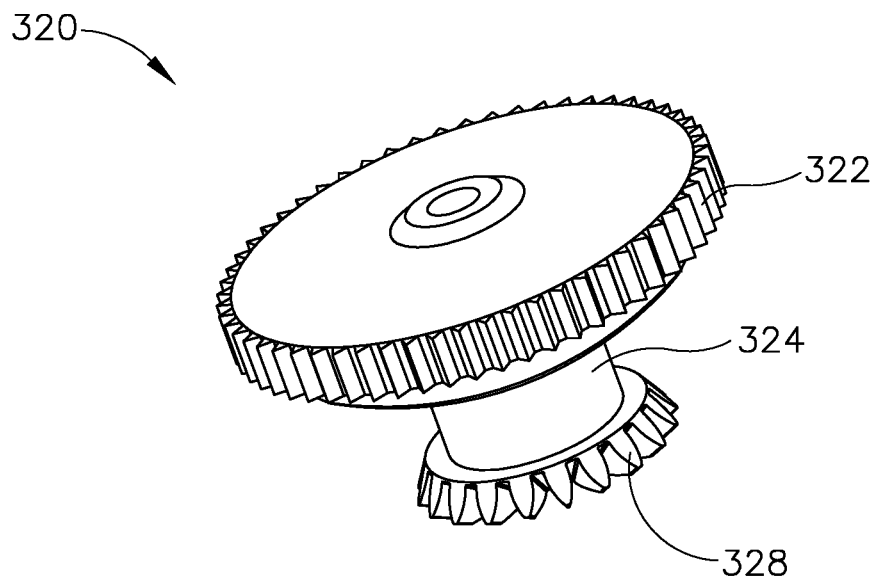
FIG. 15 depicts a perspective view of a shaft rotation control knob of the instrument of FIG. 1A.
Figure 16:
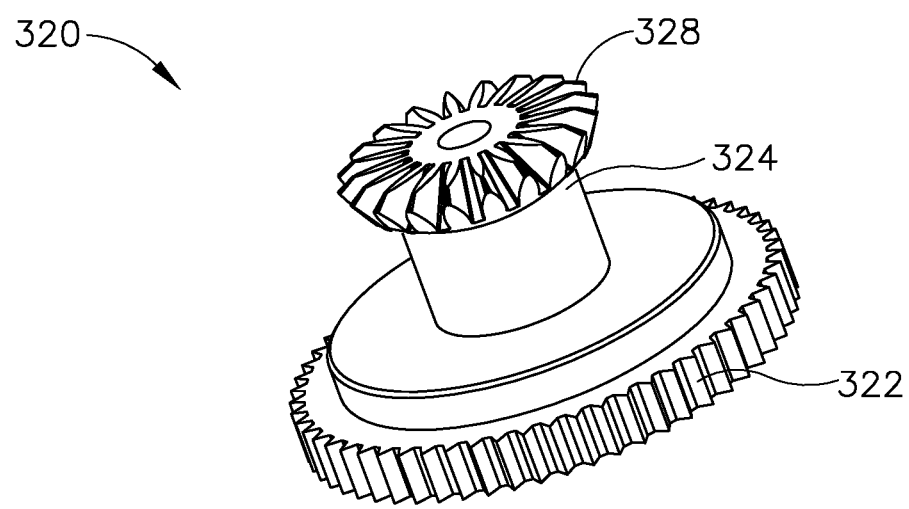
FIG. 16 depicts another perspective view of the shaft rotation control knob of FIG. 15.

In addition to providing control for the deflection of flex section (210) to facilitate access to various anatomical passageways, it may be desirable to enable rotation of shaft assembly (100) about the longitudinal axis of shaft assembly (100), to further facilitate access to various anatomical passageways. To that end, instrument (10) includes a shaft rotation control knob (320). As shown in FIGS. 15-16, shaft rotation control knob (320) includes a thumbwheel (322), a shaft (324), and a bevel gear (328). As shown in FIG. 14, shaft rotation control knob (320) is secured to housings (504) of handle assembly (500) such that thumbwheel (322) is above housings (504), with shaft (324) being captured between housings (504). Thumbwheel (322) is positioned such that an operator may rotate thumbwheel (322) relative to housings (504) using the thumb of the hand that is grasping handle assembly (500). An o-ring (324) is positioned along the exterior of shaft (324) to engage housings (504), though this is merely optional. Bevel gear (328) is positioned to engage a bevel gear (120) at the proximal end of rigid shaft member (110). Thus, when shaft rotation control knob (320) is rotated about the longitudinal axis of shaft (324) (which is perpendicular to the longitudinal axis of shaft assembly (100)), shaft assembly (100) will rotate about the longitudinal axis of shaft assembly (100) due to the meshing engagement of bevel gears (120, 328).

C. Exemplary Guidewire and Associated Actuation Assembly

FIGS. 17-22 show the various components of guidewire actuation assembly (600). These components include a spin actuator (610) and a slide actuator (650). Spin actuator (610) is operable to rotate guidewire (602) about the longitudinal axis of guidewire (602); while slide actuator (650) is operable to translate guidewire (602) along the longitudinal axis of guidewire (602).

In some versions, guidewire (602) includes one or more optical fibers and a distal end (606) that is configured to emit visible light. In some such versions, guidewire module (12) includes a light source, and connector (604) is operable to communicate light from the light source of guidewire module (12) to guidewire (602). Illuminating versions of guidewire (602) may be used to provide position confirmation through observation of transillumination effects. By way of example only, illuminating versions of guidewire (602) may be constructed and operable in accordance with at least some of the teachings of U.S. Pat. No. 9,155,492, entitled "Sinus Illumination Lightwire Device," issued Oct. 13, 2015, the disclosure of which is incorporated by reference herein.

In addition to providing illumination, or as an alternative to providing illumination, guidewire (602) may provide position sensing capabilities. In some such versions, the distal end of guidewire (602) may include a position sensor. By way of example only, such a guidewire (602) may be constructed and operable in accordance with at least some of the teachings of U.S. patent application Ser. No. 15/861,959, entitled "Navigation Guidewire with Interlocked Coils," filed Jan. 4, 2018, the disclosure of which is incorporated by reference herein; U.S. patent application Ser. No. 15/852,530, entitled "Reusable Navigation Guidewire," filed Dec. 22, 2017, the disclosure of which is incorporated by reference herein; U.S. Pub. No. 2016/0008083, entitled "Guidewire Navigation for Sinuplasty," published Jan. 14, 2016, the disclosure of which is incorporated by reference herein. In some such versions, guidewire module (12) includes an IGS navigation system, and connector (604) is operable to communicate position-indicative signals from the sensor of guidewire (602) to guidewire module (12).

In some versions, connector (604) is in the form of a slip coupling. Such a slip coupling may be configured to provide tensile strain relief for guidewire (602) while allowing guidewire (602) to freely rotate between connector (604) and any coupled components associated with guidewire module (12) (e.g., an additional cable coupled between connector (604) and guidewire module (12), etc.). This may prevent the build-up of torsion along any components that are proximal to connector (604) while guidewire (602) is rotated about the longitudinal axis of guidewire (602). By way of example only, connector (604) may be constructed and operable in accordance with at least some of the teachings of U.S. Pat. App. Ser. No. 16/032,489, entitled "Adjustable Instrument for Dilation of Anatomical Passageway," filed on even date herewith, the disclosure of which is incorporated by reference herein. In versions where guidewire (602) includes one or more optical fibers or other light-communicating features, connector (604) includes features allowing light to pass freely through connector (604), such that connector (604) maintains optical continuity between guidewire module (12) and guidewire (602). In versions where guidewire (602) includes one or more position sensors, connector (604) includes features that provide electrical continuity between guidewire module (12) and guidewire (602).

Figure 20:
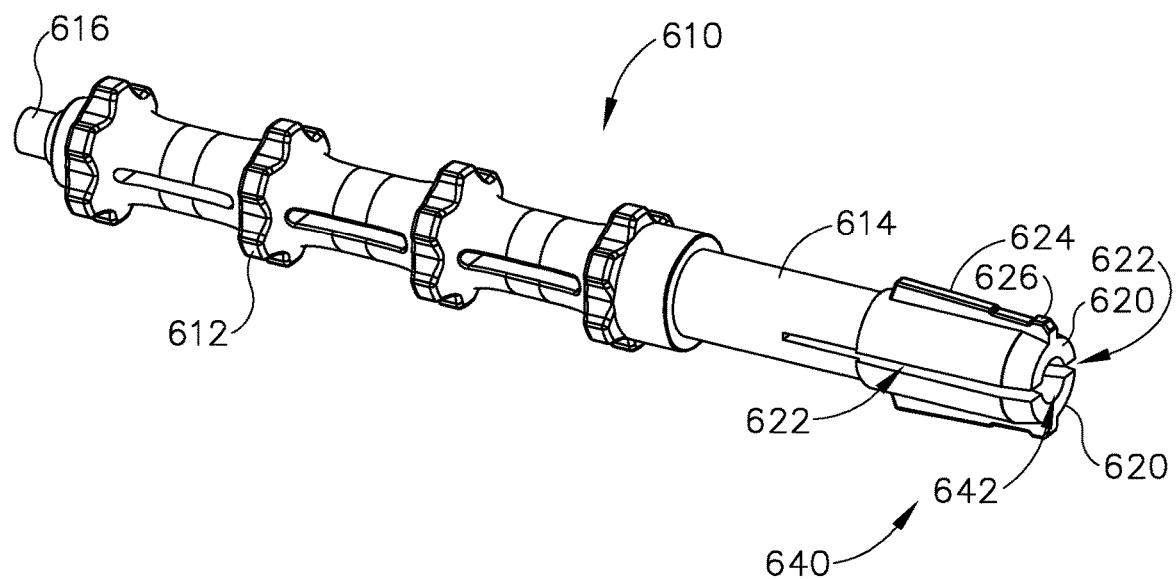
FIG. 20 depicts a perspective view of a rotation actuator of the guidewire actuation assembly of FIG. 17.

As best seen in FIG. 20, spin actuator (610) of the present example includes a plurality of thumbwheel engagement features (612), a proximal shaft (614), and a distal shaft (616). Proximal shaft (614) includes a collet chuck feature (640) formed by a pair of collet leaves (620) that are separated by diametrically opposed longitudinally extending slots (622). Slots (622) are configured to provide clearance to allow collet leaves (620) to deflect inwardly toward each other to thereby grip guidewire (602). Each collet leaf (620) includes a fin (624) extending longitudinally and radially outwardly. Each fin (624) includes a proximally positioned detent feature (626).

Figure 19:
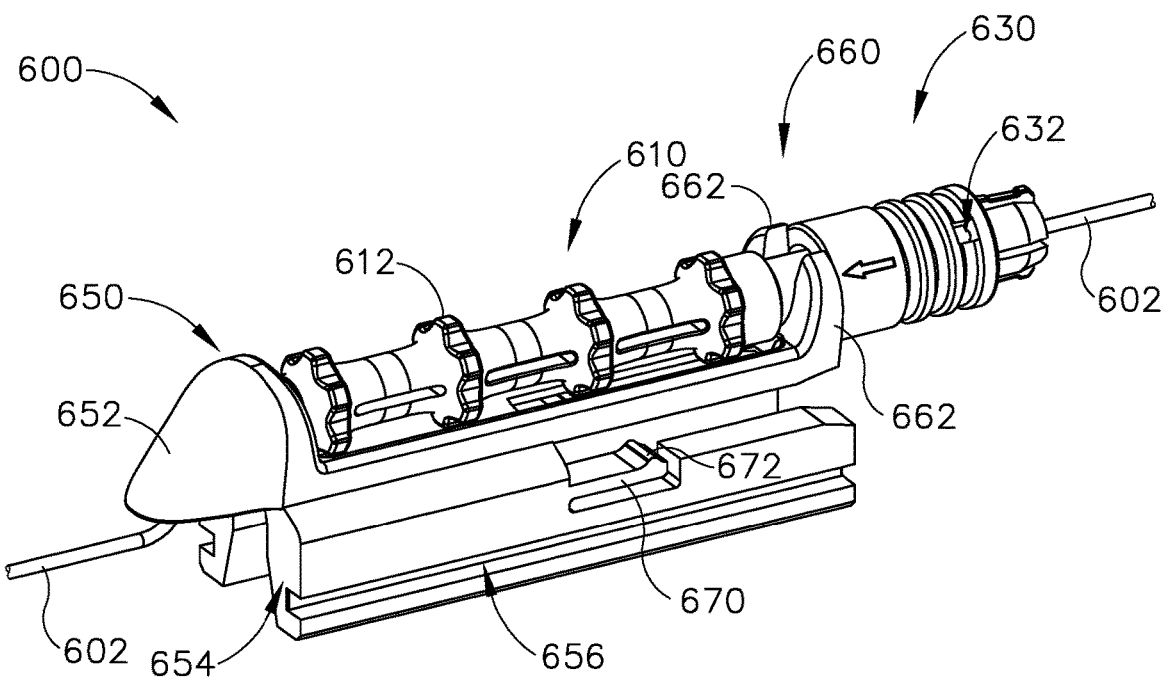
FIG. 19 depicts an enlarged perspective view of actuators of the guidewire actuation assembly of FIG. 17, with the collet collar of FIG. 18 in a distal position.
Figure 21:
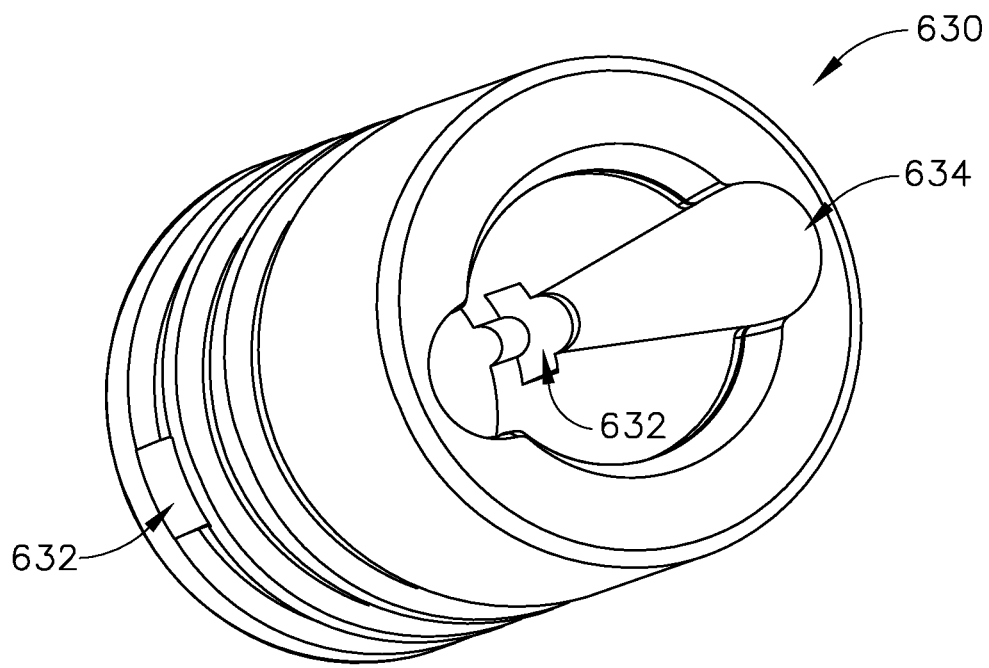
FIG. 21 depicts a perspective view of the collet collar of FIG. 18.
Figure 22:
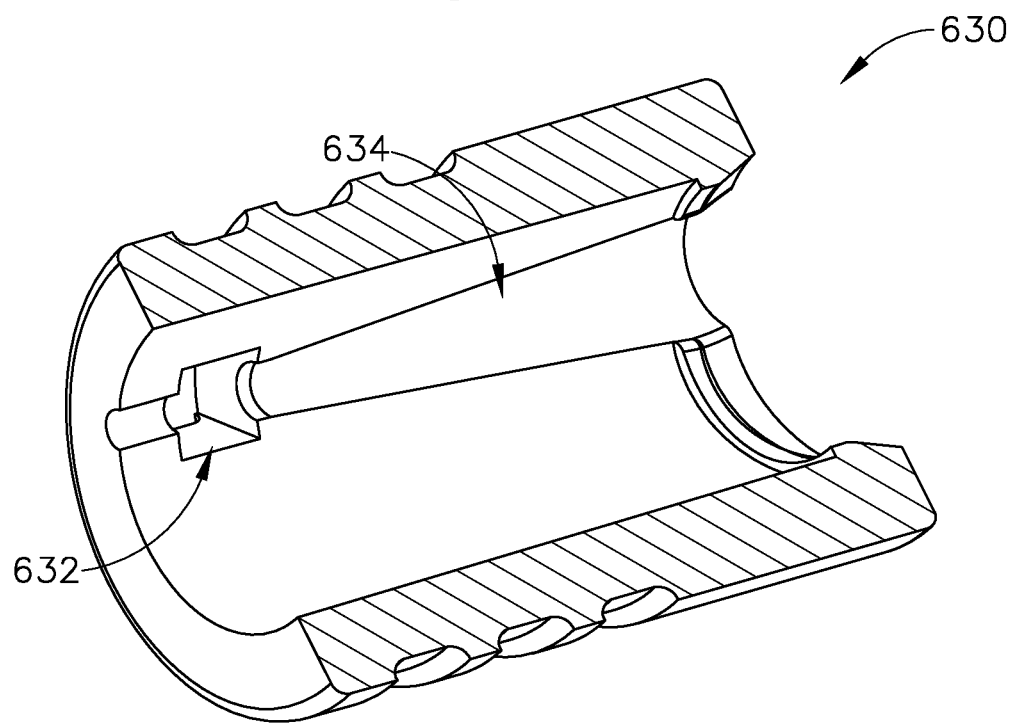
FIG. 22 depicts a cross-sectional perspective view of the collet collar of FIG. 18.

As shown in FIGS. 18-19, a collet collar (630) is configured to translate along proximal shaft (614) between a proximal position (FIG. 18) and a distal position (FIG. 19) to thereby transition collet chuck feature (640) between a locked state (FIG. 18) and an unlocked state (FIG. 19). As shown in FIGS. 21-22, collet collar (630) includes a pair of inner recesses (634) that lead to lateral notches (632). Inner recesses (634) extend longitudinally along diametrically opposed regions of the inner sidewall of collet collar (630) and have frusto-conical configurations. In the present example, each inner recess (634) tapers radially inwardly along the length of inner recess (634), such that the diametric distance between opposed distal regions of inner recesses (634) is less than the diametric distance between opposed proximal regions of inner recesses (634). Each inner recess (634) also tapers along a dimension that is perpendicular to the diametric span between inner recesses (634). The tapered configurations of inner recesses (634) provide camming to drive leaves (620) inwardly toward each other as collet collar (630) is translated from the distal position to the proximal position. The tapered configurations of inner recesses (634) also provide lead-ins to notches (632). Recesses (634) are positioned to correspond with fins (624) of collet leaves (620); and recesses (634) are sized to slidably receive fins (624). Notches (632) are configured to receive respective detent features (626) of fins (624). Detent features (626) cooperate with notches (632) to selectively maintain the longitudinal position of collet collar (630) along proximal shaft (614) when collet collar (630) is in the proximal position. Detent features (626) thus cooperate with notches (632) to selectively maintain collet chuck feature (640) in the locked state.

When collet chuck feature (640) is in the locked state, collet leaves (620) are deformed inwardly to grip guidewire (602) disposed in the central longitudinal bore (642) of spin actuator (610). When collet chuck feature (640) is in the unlocked state, collet leaves (620) resiliently return to their natural position, thereby releasing their grip on guidewire (602). Thus, when collet chuck feature (640) is in the unlocked state, the operator may selectively adjust the longitudinal position of guidewire (602) relative to spin actuator (610). In some instances, the operator may wish to remove guidewire (602) from spin actuator (610) when collet chuck feature (640) is in the unlocked state. In some such instances, the operator may wish to exchange one guidewire (602) for another guidewire (602) (e.g., to exchange an illuminating guidewire (602) for a guidewire (602) having a position sensor, or vice-versa, etc.).

As best seen in FIGS. 18-19, slide actuator (650) of the present example comprises a distal nose portion (652), a lower base portion (654), and a proximal yoke (660). Distal nose portion (652) is configured to rotatably support distal shaft (615) of spin actuator (610). Proximal yoke (660) includes a pair of fork tines (662) that are configured to rotatably support proximal shaft (614) of spin actuator (610). Lower base portion (654) includes a pair of longitudinally extending recesses (656) that are configured to slidably receive corresponding rails (not shown) defined by housings (540) of handle assembly (500). Slide actuator (650) is operable to slide longitudinally relative to housings (540), to thereby translate guidewire (602) and spin actuator (610) longitudinally, while also allowing spin actuator (610) to rotate guidewire (602) relative to slide actuator (650). Distal nose portion (652) is also configured to redirect guidewire (602) from a first longitudinal axis (associated with the proximal portion of guidewire (602)) to a second longitudinal axis (associated with dilation catheter (702) and the distal portion of guidewire (602)), with the second longitudinal axis being parallel with the first longitudinal axis. Lower base portion (654) also includes a pair of upwardly extending detent features (672) positioned on proximal ends of corresponding cantilever arms (670). Detent features (672) will be described in greater detail below.

As noted above with reference to FIGS. 1A-1B, an operator may translate guidewire (602) longitudinally relative to handle assembly (500) by engaging guidewire actuation assembly (600) and sliding guidewire actuation assembly (600) longitudinally along handle assembly (500). Due to the position and configuration of guidewire actuation assembly (600), the operator may accomplish such motion by simply engaging guidewire actuation assembly (600) with the thumb (or another finger) of the hand that is grasping handle assembly (500). In some instances, the operator may also wish to rotate guidewire (602) about the longitudinal axis of guidewire (602). This may be particularly desirable when the distal end of guidewire (602) includes a preformed bend, as rotation of guidewire (602) may be used to advantageously reorient the bent distal end of guidewire (602) to thereby align the bent distal end of guidewire (602) with a targeted passageway. To provide such rotation, the operator may engage one or more thumbwheel engagement features (612) with the thumb (or another finger) of the hand that is grasping handle assembly (500). Guidewire actuation assembly (600) is thus configured to facilitate single-handed use including translation and rotation of guidewire (602). The elongate configuration of guidewire actuation assembly (600) may further facilitate single-handed use regardless of whether guidewire actuation assembly (600) is positioned distally or proximally along handle assembly (500).

D. Exemplary Dilation Catheter and Associated Actuation Assembly

FIGS. 23-26C show various components of catheter actuation assembly (700). These components include a slide actuator (740) that is fixedly secured to dilation catheter (702). Slide actuator (740) has an arched configuration that allows slide actuator (740) to freely pass over the top of guidewire actuation assembly (600) when one actuation assembly (600, 700) is translated relative to the other actuation assembly (600, 700). Slide actuator (740) includes a lower base portion (742) that defines a pair of longitudinally extending recesses (744) that are configured to slidably receive corresponding rails (not shown) defined by housings (540) of handle assembly (500). Slide actuator (740) is thus operable to slide longitudinally relative to housings (540), to thereby translate dilation catheter (702) longitudinally.

As shown in FIGS. 1A-ID and 23, the proximal end of dilation catheter (702) includes a connector (710). Connector (710) includes an inflation port (712) that is configured to couple with an inflation fluid source (14), and an irrigation port (714) that is configured to couple with an irrigation fluid source (16). Ports (712, 714) may be configured as conventional luer features. By way of further example only, connector (710) may be connected and operable in accordance with at least some of the teachings of U.S. Pat. App. No. 62/640,598, entitled "Fluid Fitting for Dilation Instrument," filed Mar. 9, 2018, the disclosure of which is incorporated by reference herein.

Inflation fluid source (14) is operable to provide an inflation fluid (e.g., saline) via inflation port (712) to selectively inflate and deflate dilator (722) of dilation catheter (702). In some versions, inflation fluid source (14) is constructed and operable in accordance with at least some of the teachings of U.S. Pat. No. 9,962,530, entitled "Inflator for Dilation of Anatomical Passageway," issued May 8, 2018, the disclosure of which is incorporated by reference herein. As another merely illustrative example, inflation fluid source (14) may be constructed and operable in accordance with at least some of the teachings of U.S. Pub. No. 2016/0058985, entitled "Automated Inflator for Balloon Dilator," published Mar. 3, 2016, the disclosure of which is incorporated by reference herein. Other suitable forms that inflation fluid source (14) may take will be apparent to those skilled in the art in view of the teachings herein.

In addition to being capable of providing dilation, dilation catheter (702) of the present example is also configured to provide irrigation of a site within a patient. By way of example only, dilation catheter (702) may be constructed and operable in accordance with at least some of the teachings of U.S. Pat. No. 9,095,646, entitled "Devices and Methods for Transnasal Dilation and Irrigation of the Sinuses," issued Aug. 4, 2015, the disclosure of which is incorporated by reference herein. Dilation catheter (702) receives irrigation fluid (e.g., saline) from irrigation fluid source (16) via irrigation port (714) of connector (710) as described above. By way of example only, irrigation fluid source (16) may provide gravity-fed irrigation fluid, may include a syringe, may include an electrically activated pump, or may take any other suitable form as will be apparent to those skilled in the art in view of the teachings herein.

In some other versions, rather than dilation catheter (702) having irrigation capabilities, a dedicated irrigation catheter may be used. By way of example only, a dedicated irrigation catheter may be configured and operable in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, the disclosure of which is incorporated by reference herein.

Figure 23:
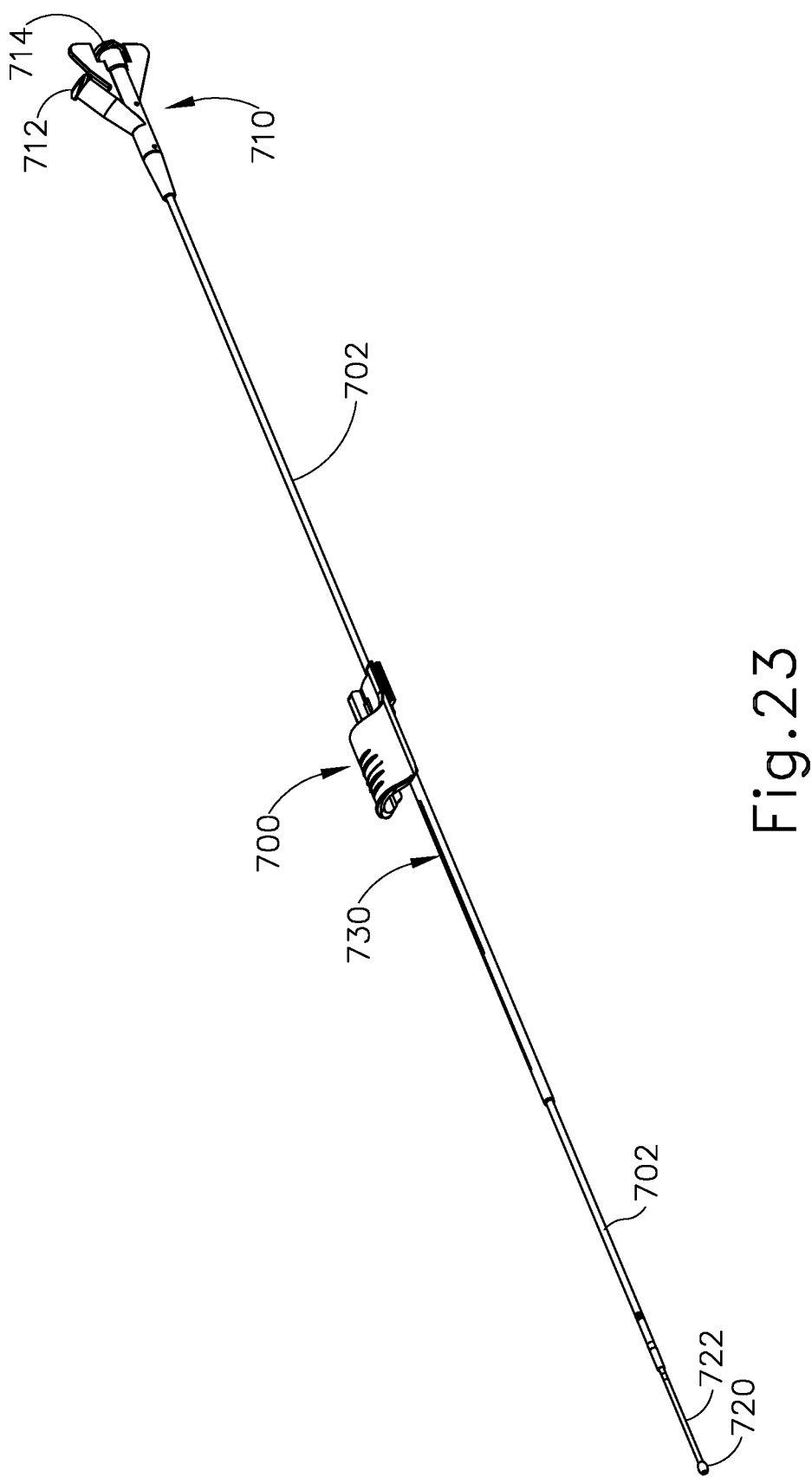
FIG. 23 depicts a perspective view of a dilation catheter actuation assembly of the instrument of FIG. 1A.
Figure 24:
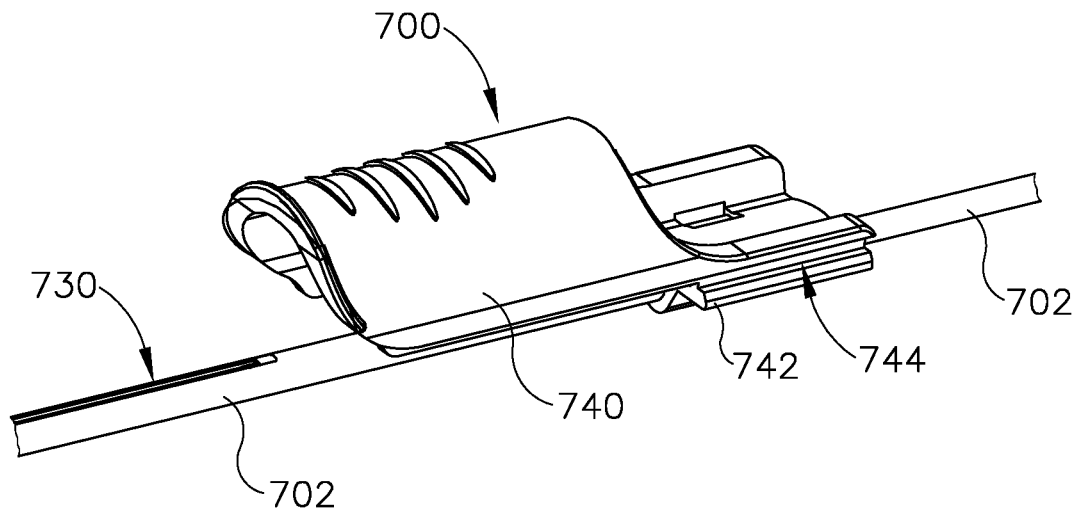
FIG. 24 depicts an enlarged perspective view of an actuator of the dilation catheter actuation assembly of FIG. 23.

As shown in FIGS. 23-24, dilation catheter (702) of the present example includes a lateral slit (730) that is configured to receive guidewire (602). As noted above, distal nose portion (652) of guidewire slide actuator (650) redirects guidewire (620) downwardly from a longitudinal axis associated with the proximal portion of guidewire (620). In the present example, distal nose portion (652) directs guidewire (620) to enter dilation catheter (702) vial lateral slit (730), thereby positioning the distal portion of guidewire (620) along the central longitudinal axis of dilation catheter (702). This may be accomplished without compromising the integrity of an inflation lumen (not shown) of dilation catheter (702), such that the inflation lumen of dilation catheter (702) may be fluidly isolated relative to the lumen of dilation catheter (702) that receives guidewire (602), even with lateral slit (730) present. Various suitable configurations for accomplishing this will be apparent to those skilled in the art in view of the teachings herein. Lateral slit (730) of the present example is elongated to accommodate translation of guidewire (602) relative to dilation catheter (702).

Figure 26A:
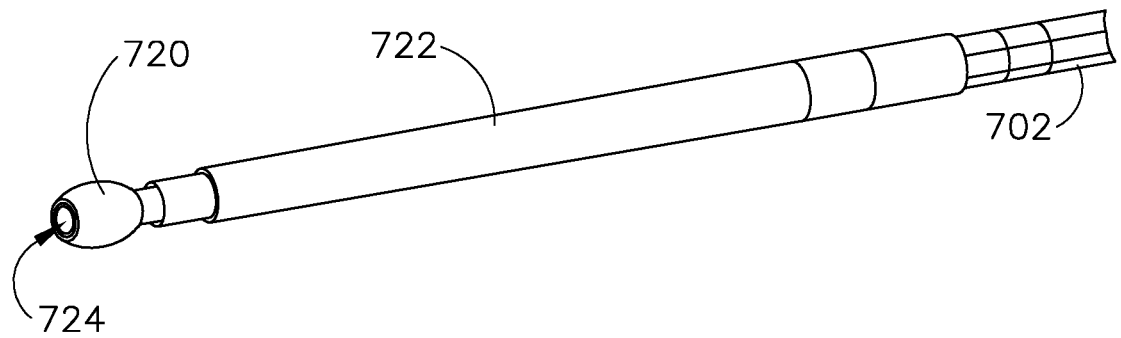
FIG. 26A depicts a perspective view of a distal portion of a dilation catheter of the instrument of FIG. 1A, with a distal tip in an expanded state, and with a dilator in the non-expanded state.
Figure 26B:
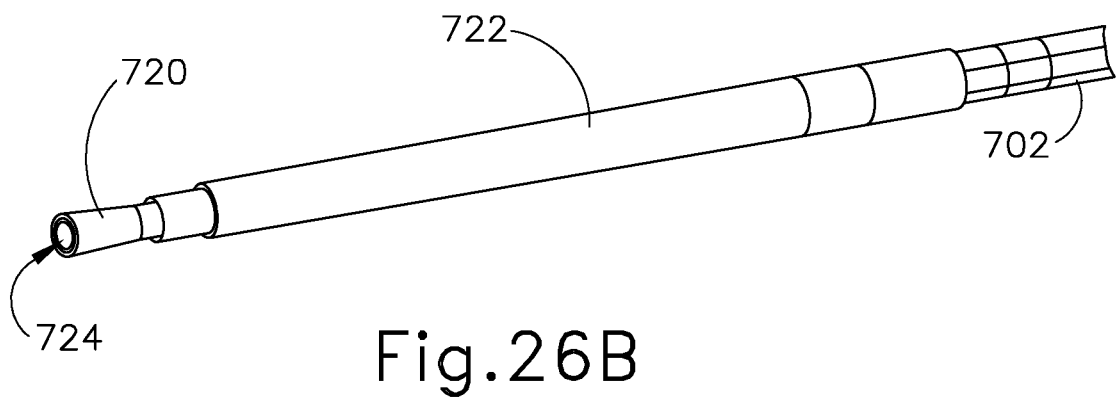
FIG. 26B depicts a perspective view of the distal portion of FIG. 26A, with the distal tip in a non-expanded state, and with the dilator in the non-expanded state.
Figure 26C:
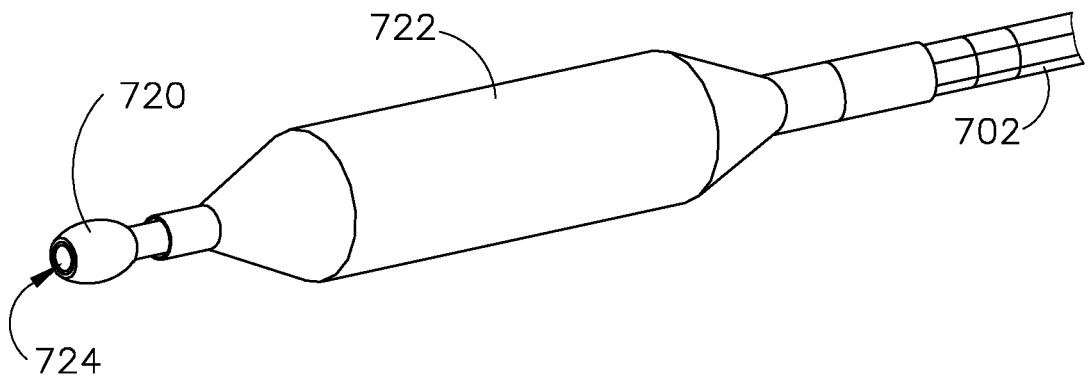
FIG. 26C depicts a perspective view of the distal portion of FIG. 26A with the distal tip in the expanded state, and with the dilator in the expanded state.

FIGS. 26A-26C show the distal end of dilation catheter (702) in greater detail. As shown, dilation catheter (702) of this example comprises a distal tip (720) and an expandable dilator (722) located proximal to distal tip (720). Distal tip (720) defines an opening (724) that is sized to accommodate guidewire (602). Distal tip (720) is resiliently bias to assume the expanded configuration shown in FIGS. 26A and 26C. However, distal tip (720) is also configured to collapse to the non-expanded state shown in FIG. 26B, when sufficient inwardly-oriented forces act upon distal tip (720). Dilator (722) is configured to expand from the non-expanded state shown in FIGS. 26A-26B to the expanded state shown in FIG. 26C, based on the transfer of inflation fluid into and out of dilator (722) as described above.

During operation, dilation catheter (702) may be advanced into the targeted anatomical passageway while in the configuration shown in FIG. 26A. If the targeted anatomical passageway is the Eustachian tube, distal tip (720) will eventually encounter the bony isthmus near the middle ear. Distal tip (720) is larger than the isthmus of the Eustachian tube, such that the operator will feel resistance to further advancement of dilation catheter (702) once distal tip (720) reaches the isthmus of the Eustachian tube. Because it may be undesirable for distal tip (720) to reach the middle ear, the operator may immediately cease advancement of dilation catheter (702) and expand dilator (722) to reach the state shown in FIG. 26C, thereby dilating the Eustachian tube.

In scenarios where the targeted anatomical passageway is not a Eustachian tube, distal tip (720) may eventually encounter a passageway that is smaller than distal tip (720). For instance, distal tip (720) may encounter a paranasal sinus ostium. In such scenarios, the operator may continue to urge distal tip (720) through the passageway, which will cause distal tip (720) to collapse to the configuration shown in FIG. 26B. Eventually, distal tip (720) will clear the passageway and re-expand; and dilator (722) will be positioned in the passageway. At this point, the operator may expand dilator (722) to reach the state shown in FIG. 26C.

In some variations, distal tip (720) is selectively expandable and collapsible based on the introduction or evacuation of fluid to or from distal tip (720). By way of example only, such variations may be constructed and operable in accordance with at least some of the teachings of U.S. Pub. No. 2017/0056632, entitled "Dilation Catheter with Expandable Stop Element," published Mar. 2, 2017, the disclosure of which is incorporated by reference herein. In some other variations, distal tip (720) does not have a bulbous configuration and is simply narrow (e.g., like the configuration shown in FIG. 26B).

Figure 1C:
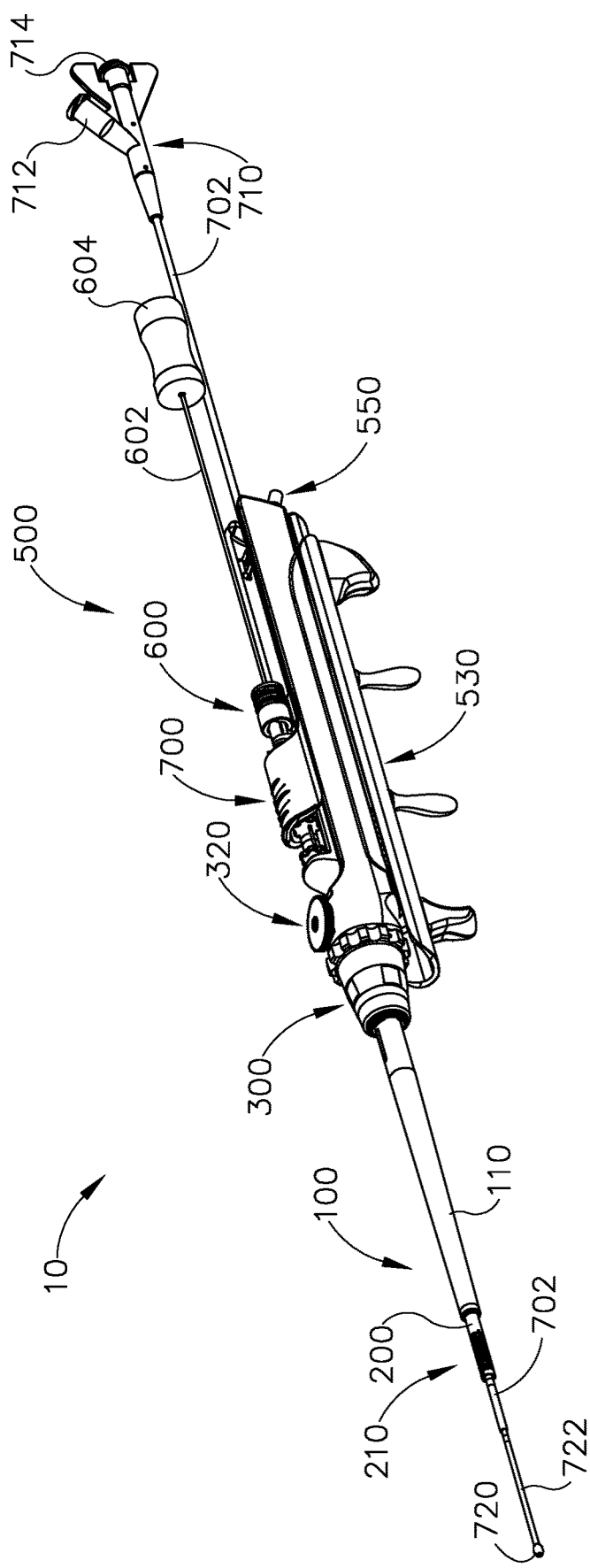
FIG. 1C depicts a perspective view of the instrument of FIG. 1A, with the guidewire and the dilation catheter each in respective distal positions, and with a dilator of the dilation catheter in a non-expanded state.
Figure 1D:
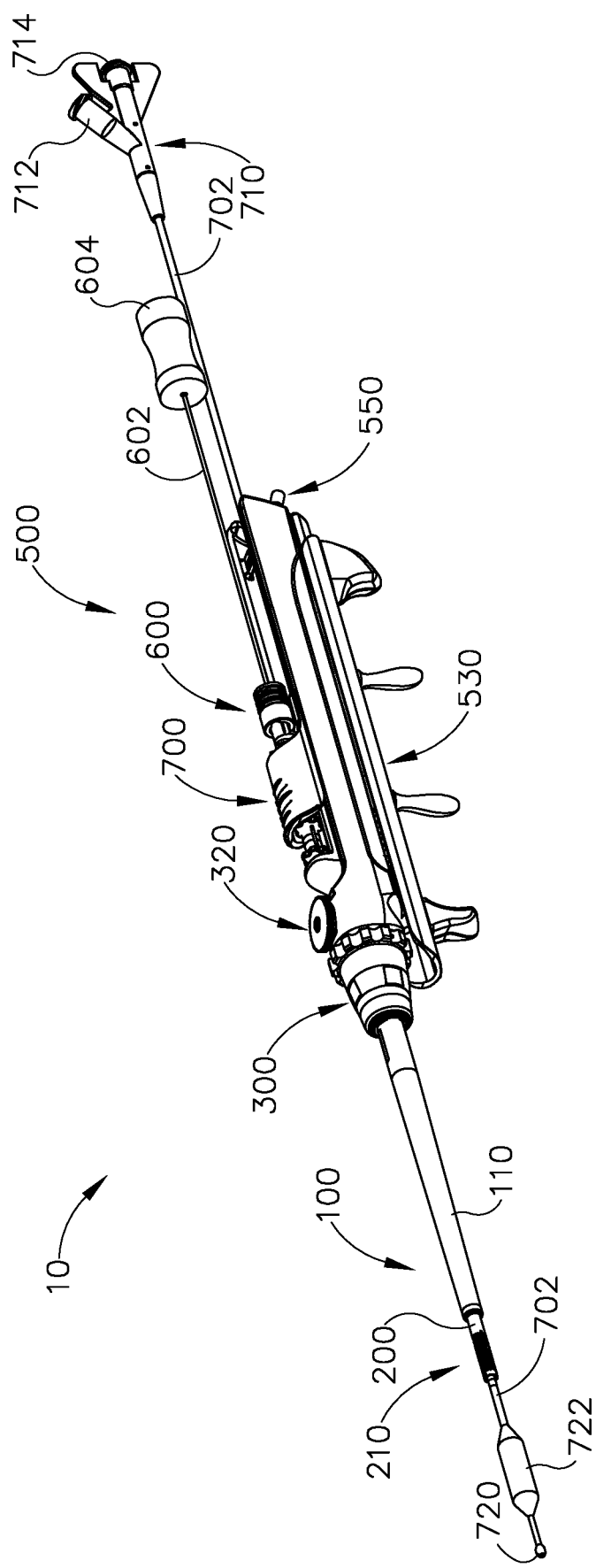
FIG. 1D depicts a perspective view of the instrument of FIG. 1A, with the guidewire and the dilation catheter each in respective distal positions, and with a dilator of the dilation catheter in an expanded state.
Figure 25:
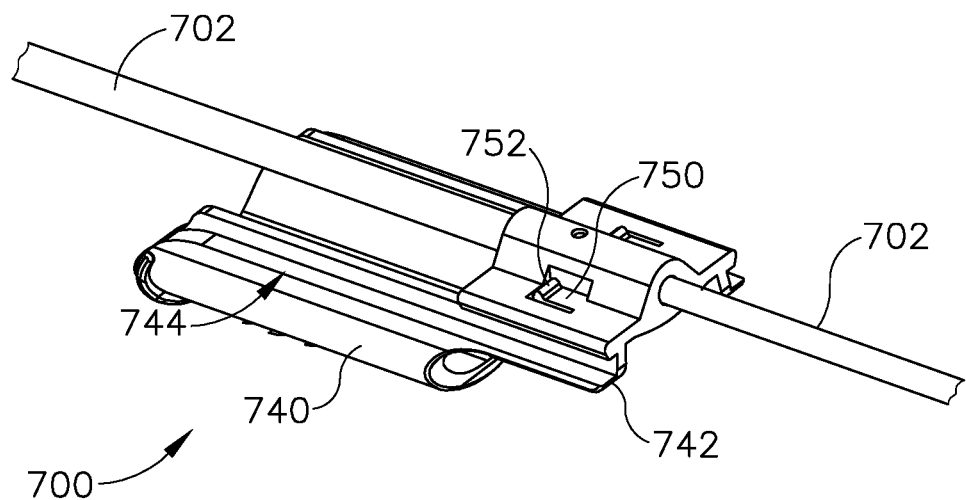
FIG. 25 depicts another enlarged perspective view of the actuator of FIG. 24.

As shown in FIG. 25, the underside of lower base portion (742) of slide actuator (740) includes a pair of downwardly projecting detent features (752) positioned on proximal ends of corresponding cantilever arms (750). Detent features (752) of slide actuator (740) are positioned and configured to engage detent features (672) of slide actuator (650). As noted above, slide actuators (650, 740) are configured to slide along housings (540) independently of each other. However, when both slide actuators (650, 740) are distally positioned as shown in FIGS. 1C-1D, the operator may eventually wish to translate slide actuators (650, 740) proximally simultaneously. To that end, detent features (672, 752) are configured to engage each other when both slide actuators (650, 740) are distally positioned as shown in FIGS. 1C-1D, such that the operator may simply engage slide actuator (740) with a thumb or finger (without needing to directly engage guidewire actuation assembly (600) with a thumb or finger) to translate slide actuators (650, 740) proximally simultaneously. The engagement between detent features (672, 752) may provide simultaneous proximal translation of slide actuators (650, 740), thereby providing simultaneous proximal translation of guidewire (602, 702), in response to the operator directly driving slide actuator (740) proximally. The operator may also selectively disengage detent features (672, 752) by translating one slide actuator (650, 740) while holding the other slide actuator (650, 740) stationary.

In some variations, the operator may adjust the longitudinal position of guidewire (602) relative to guidewire actuation assembly (600) such that distal end (606) of guidewire (602) will always protrude distally past distal tip (720) of dilation catheter (702); even when both slide actuators (650, 740) are in the proximal position shown in FIG. 1A. In such versions, distal end (606) may still be positioned proximal to distal end (202) of guide shaft assembly (100) when both slide actuators (650, 740) are in the proximal position shown in FIG. 1A. In some such versions, detent features (672, 752) may be positioned and configure to engage with each other even when both slide actuators (650, 740) are in the proximal position shown in FIG. 1A. In such versions, the operator may simply engage slide actuator (740) with a thumb or finger (without needing to directly engage guidewire actuation assembly (600) with a thumb or finger) to translate slide actuators (650, 740) distally simultaneously. The engagement between detent features (672, 752) may provide simultaneous distal translation of slide actuators (650, 740), thereby providing simultaneous distal translation of guidewire (602, 702), in response to the operator directly driving slide actuator (740) distally.

Versions where detent features (672, 752) provide simultaneous distal translation of slide actuators (650, 740) may still also provide simultaneous proximal translation of slide actuators (650, 740). For instance, when both slide actuators (650, 740) are in the proximal position shown in FIG. 1A, the distal faces of detent features (752) may engage the proximal faces of detent features (672) and may bear thereagainst during distal translation of slide actuator (740) to thereby drive slide actuator (650) distally as slide actuator (740) is pushed distally by the operator. After slide actuators (650, 740) both reach the distal-most position, a boss feature of housings (540) may arrest further distal translation of slide actuator (650) while permitting slight further distal translation of slide actuator (740). The operator may thus urge slide actuator (740) slightly distally further relative to slide actuator (650), such that detent features (752) slide over the peaks of detent features (672), causing cantilever arms (750) and/or cantilever arms (670) to deflect, until the proximal faces of detent features (752) reach the distal faces of detent features (672). Then, when the operator urges slide actuator (740) back to the proximal position, the proximal faces of detent features (752) may bear against the distal faces of detent features (672) to thereby drive slide actuator (650) distally as slide actuator (740) is pulled proximally by the operator.

After slide actuators (650, 740) both reach the proximal-most position, a boss feature of housings (540) may arrest further proximal translation of slide actuator (650) while permitting slight further proximal translation of slide actuator (740). The operator may thus urge slide actuator (740) slightly proximally further relative to slide actuator (650), such that detent features (752) again slide over the peaks of detent features (672), causing cantilever arms (750) and/or cantilever arms (670) to deflect, until the distal faces of detent features (752) reach the proximal faces of detent features (672). The foregoing process may thus be used to provide single-handed simultaneous distal and proximal translation of guidewire (602) and dilation catheter (702), while still permitting the operator to provide independent translation if desired (by actively disengaging detent features (672, 752).

As another merely illustrative variation, housings (540) may provide one or more detent features (not shown) to selectively retain at least one slide actuator (650, 740) when the at least one slide actuator (650, 740) is at the proximal position shown in FIG. 1A. The selective retention of at least one slide actuator (650, 740) by the detent feature(s) of housings (540) may prevent or defeat engagement between detent features (672, 752) when the at least one slide actuator (650, 740) is at the proximal position shown in FIG. 1A. Various suitable forms that such detent features may take will be apparent to those skilled in the art in view of the teachings herein. Alternatively, such detent features may be omitted from housings (540). Detent features (672, 752) may also be omitted if desired.

E. Other Exemplary Features of Handle Assembly

Figure 27:
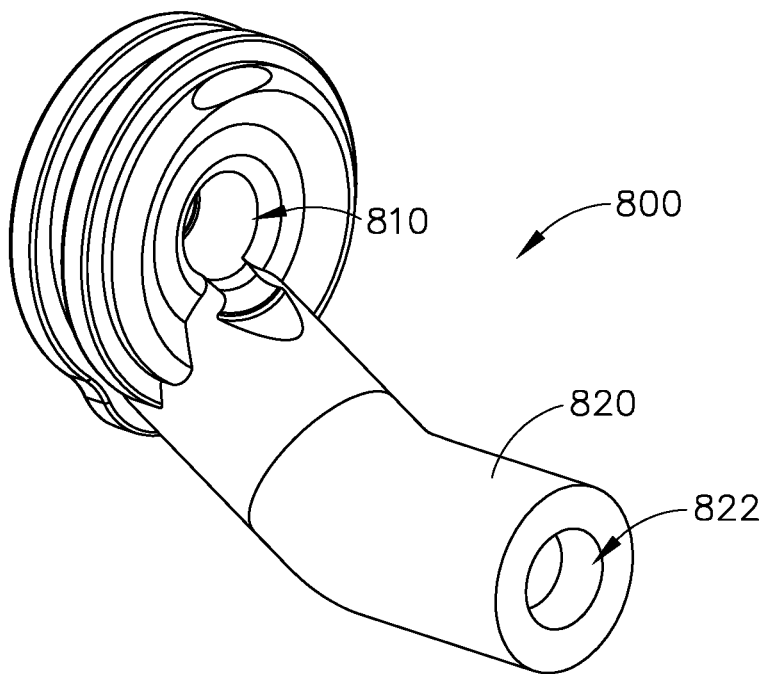
FIG. 27 depicts a perspective view of a suction manifold of the instrument of FIG. 1A.
Figure 28:
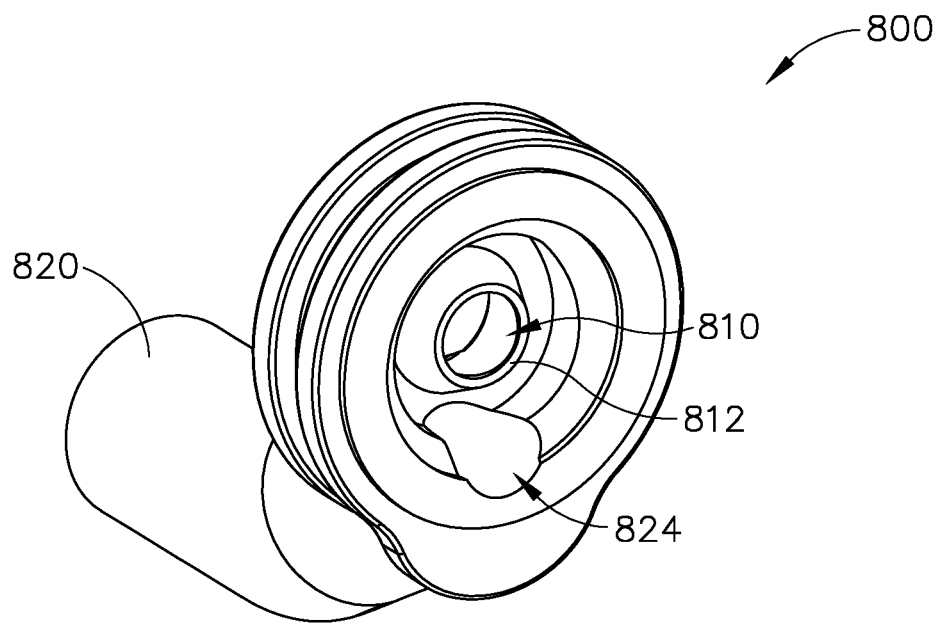
FIG. 28 depicts another perspective view of the suction manifold of FIG. 27.

As shown in FIG. 14, a suction manifold (800) is positioned in handle assembly (500). As shown in FIGS. 27-28, suction manifold (800) of this example includes a first opening (810) that is surrounded by a frusto-conical dynamic seal (812). Suction manifold also includes a conduit (820) having a proximal opening (822) in fluid communication with a distal opening (824). Distal opening (824) is positioned below first opening (810). Referring back to FIG. 14, first opening (810) is coaxial with dilation catheter (702), with dilation catheter (702) passing through first opening (810). Dynamic seal (812) contacts the exterior of dilation catheter (702) and thereby forms a fluid seal against the exterior of dilation catheter (702). Dynamic seal (812) nevertheless permits longitudinal translation of dilation catheter (702) relative to suction manifold (800).

Suction conduit (802) is coupled with proximal opening (822) of manifold (800). As noted above with reference to FIG. 1, a suction source (18) is coupled with suction conduit (802). Suction source (18) may comprise any suitable source of suction, including but not limited to a vacuum pump, a syringe, or any other suitable kind of suction source as will be apparent to those skilled in the art in view of the teachings herein. Suction from suction source (18) is communicated via suction conduit (802) to conduit (820), thereby reaching distal opening (824) of conduit (820). Suction at distal opening (824) is further communicated to shaft assembly (100). For instance, shaft assembly (100) may have an inner diameter that is sized such that a gap is present between the inner diameter of shaft assembly (100) and the outer diameter of dilation catheter (702), and the suction from distal opening (824) may reach the distal end of shaft assembly (100) via the gap between the inner diameter of shaft assembly (100) and the outer diameter of dilation catheter (702). The suction from distal opening (824) may reach this gap via an interior space defined by housings (504) of handle assembly (500), between the distal end of manifold (800) and the proximal end of shaft assembly (100). Other suitable ways in which suction may be communicated to the distal end of shaft assembly (100) will be apparent to those skilled in the art in view of the teachings herein.

In some versions, one or both housings (504) defines a vent port (not shown) that may be selectively covered or uncovered by a finger of the operator's hand that grasps handle assembly (500). Such a vent port may be in fluid communication with the interior space defined by housings (504) of handle assembly (500) between the distal end of manifold (800) and the proximal end of shaft assembly (100). Such a vent port may allow the operator to selectively apply suction. In scenarios where suction is not desired, the operator may simply leave the vent port uncovered. When the vent port is uncovered, suction that is drawn via suction conduit (802) and manifold (800) will simply be applied to atmosphere via the uncovered vent port. In scenarios where suction is desired, the operator may cover the vent port with a finger of the hand grasping handle assembly (500). When the vent port is covered, suction that is drawn via suction conduit (802) and manifold (800) will be applied to the target site via shaft assembly (100). In some variations, these suction features are simply omitted.

Depending on the position of the patient and the personal preference of the operator, an operator may wish to manipulate an instrument using various kinds of grasping techniques. For instance, some operators in some scenarios may wish to grasp an instrument using a power grip. Alternatively, some operators in some scenarios may wish to grasp an instrument using a pencil grip. In addition, even within the same category of grip (e.g., power grip), the hand size or general preference of an operator may warrant selectability in the structural configuration of the structure that the operator will be grasping. To that end, handle assembly (500) of the present example includes features that allow the operator to change the structural configuration of handle assembly (500) to accommodate or otherwise facilitate different grasping configurations and techniques. In particular, and as shown in FIG. 29, handle assembly (500) of the present example comprises a pair of housings (540) that are removably coupled with a grip portion (530). Housings (540) are fixedly secured together to provide a unitary handle assembly (500) even in instances where grip portion (530) is removed.

As shown in FIG. 30, housings (540) define lateral slots (542) extending along the length of housings (540). Lateral slots (542) each include a longitudinally spaced array of teeth (544). As shown in FIG. 29, grip portion (530) includes a plurality of downwardly projecting protrusions (532). Protrusions (532) may be positioned between fingers of the hand grasping handle assembly (500) to promote a firm grip on handle assembly (500). As shown in FIG. 31, grip portion (530) further includes a pair of inwardly protruding rails (534) extending along the length of grip portion (530). Rails (534) are configured to complement lateral slots (542), such that rails (534) may be slidably received in slots (542). Rails (534) each include a longitudinally spaced array of recesses (536). Recesses (536) are configured to complement teeth (544). As grip portion (530) is slid into engagement with housings (540), with rails (534) sliding along slots (542), teeth (544) ratchet along recesses (536). Teeth (544) and recesses (536) cooperate to retain the longitudinal position of grip portion (530) along housings (540) when the operator ceases translation of grip portion (530) along housings (540). Teeth (544) and recesses (536) nevertheless permit the removal of grip portion (530) from housings (540) when the operator exerts sufficient force on grip portion (530) to translate grip portion (530) relative to housings (540).

Grip portion (530) and housings (540) are thus configured to facilitate selective coupling and removal of grip portion (530) from housings (540) based on the operator's desire to use instrument (10) with or without grip portion (530). The selective nature of the coupling between grip portion (530) and housings (540) may promote use of modular forms of grip portion (530). In other words, the operator may be presented with various kinds of grip portions (530) that accommodate different hand sizes and/or gripping techniques, and the operator may choose from this selection and secure the selected grip portion (530) to housings (540) as desired. Other suitable ways in which grip portion (530) may be selectively coupled with housings (540) will be apparent to those of ordinary skill in the art in view of the teachings herein.

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft assembly extending distally from the body, wherein the shaft assembly comprises: (i) a rigid proximal portion, and (ii) a flexible distal portion; (c) a deflection actuation assembly comprising: (i) a first rotary actuator, (ii) first translatable actuation member at least partially disposed within the first rotary actuator, and (iii) a second translatable actuation member extending through the shaft assembly, wherein the second translatable actuation member couples the first translatable actuation member with the flexible distal portion of the shaft assembly, wherein the first rotary actuator is rotatable about a longitudinal axis to thereby drive the first and second translatable actuation members longitudinally, wherein the flexible distal portion is configured to deflect away from the longitudinal axis in response to translation of the first and second translatable actuation members longitudinally; and (d) a dilation catheter, wherein the dilation catheter is slidable relative to the shaft assembly, wherein the dilation catheter comprises an expandable dilator.

Example 2

The apparatus of Example 1, wherein the deflection actuation assembly further comprises a cam follower fixedly secured to the first rotary actuator, wherein the first translatable actuation member comprises a cam channel, wherein the cam follower is disposed in the cam channel.

Example 3

The apparatus of Example 2, wherein the cam channel has a helical configuration.

Example 4

The apparatus of any one or more of Examples 2 through 3, wherein the cam channel has a plurality of channel portions, wherein the channel portions are in communication with each other, wherein the cam channel further includes detent features providing transitions between the channel portions.

Example 5

The apparatus of Example 4, wherein the detent features of the cam channel are positioned at locations corresponding to predetermined deflection angles of the flexible distal portion of the shaft assembly.

Example 6

The apparatus of any one or more of Examples 1 through 5, wherein the first translatable actuation member is coaxially and slidably disposed about a proximal end of the rigid proximal portion of the shaft assembly.

Example 7

The apparatus of Example 6, wherein the first translatable actuation member and the rigid proximal portion of the shaft assembly comprise complementary features permitting the translatable actuation member to slide along the rigid proximal portion while preventing the translatable actuation member from rotating about the rigid proximal portion.

Example 8

The apparatus of any one or more of Examples 1 through 7, wherein the dilation catheter further comprises: (i) a shaft having an outer diameter, and (ii) a bulbous tip feature, wherein the bulbous tip feature is located distal to the dilator, wherein the bulbous tip feature has a width greater than the outer diameter of the shaft.

Example 9

The apparatus of Example 8, wherein the bulbous tip is deformable to reduce the width of the bulbous tip feature in response to inwardly directed forces exerted on the bulbous tip feature.

Example 10

The apparatus of any one or more of Examples 1 through 9, further comprising a guidewire, wherein the guidewire is slidably disposed in the dilation catheter.

Example 11

The apparatus of Example 10, further comprising a guidewire actuation assembly, wherein the guidewire actuation assembly is operable to translate the guidewire relative to the body, wherein the guidewire actuation assembly is further operable to rotate the guidewire about the longitudinal axis.

Example 12

The apparatus of Example 11, wherein the guidewire actuation assembly comprises a collet assembly, wherein the collet assembly is operable to selectively secure a longitudinal position of the guidewire relative to the guidewire actuation assembly.

Example 13

The apparatus of any one or more of Examples 1 through 12, wherein the body comprises a body portion and a grip portion, wherein the grip portion is selectively removable from the body portion.

Example 14

The apparatus of Example 13, wherein the body portion and the grip portion include complementary rail and recess features that are configured to provide sliding longitudinal engagement between the body portion and the grip portion, wherein the body portion and the grip portion further include complementary detent features that are configured to selectively maintain a longitudinal position of the grip portion relative to the body portion.

Example 15

The apparatus of any one or more of Examples 1 through 14, further comprising a shaft rotation assembly, wherein the shaft rotation assembly is operable to rotate the shaft assembly about the longitudinal axis.

Example 16

The apparatus of Example 15, wherein the shaft rotation assembly comprises a second rotary actuator positioned at a distal portion of the body, wherein the second rotary actuator is rotatable about an axis that is perpendicular to the longitudinal axis.

Example 17

The apparatus of any one or more of Examples 1 through 16, wherein the second translatable actuation member comprises a pull-wire.

Example 18

The apparatus of Example 17, wherein the first translatable actuation member comprises a cam barrel, wherein a proximal end of the pull-wire is secured to the cam barrel, wherein a distal end of the pull-wire is secured to a distal end of the flexible distal portion.

Example 19

An apparatus comprising: (a) a body; (b) a shaft assembly extending distally from the body, wherein the shaft assembly defines a longitudinal axis; (c) a dilation catheter, wherein the dilation catheter is slidable relative to the shaft assembly, wherein the dilation catheter comprises an expandable dilator; (d) a guidewire, wherein the guidewire is slidable relative to the shaft assembly; and (e) a shaft rotation actuator, wherein the shaft rotation actuator is rotatable about an axis of rotation that is perpendicular to the longitudinal axis of the shaft assembly, wherein the shaft rotation actuator is operable to rotate the shaft assembly about the longitudinal axis of the shaft assembly in response to rotation of the shaft rotation actuator about the axis of rotation that is perpendicular to the longitudinal axis of the shaft assembly.

Example 20

An apparatus comprising: (a) an instrument body: (b) a shaft assembly extending distally from the instrument body; (c) a dilation catheter, wherein the dilation catheter is slidable relative to the shaft assembly, wherein the dilation catheter comprises an expandable dilator; (d) a guidewire, wherein the guidewire is slidable relative to the shaft assembly; and (e) a guidewire rotation drive assembly, wherein the guidewire rotation drive assembly is configured to selectively grip the guidewire and thereby rotate the guidewire about a longitudinal axis of the guidewire, wherein the guidewire rotation drive assembly is further configured to selectively release the guidewire and thereby enable the guidewire to translate longitudinally through the guidewire rotation drive assembly.

III. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus, comprising:
(a) a body;
(b) a shaft assembly extending distally from the body and defining a longitudinal axis, wherein the shaft assembly comprises:
   (i) a rigid proximal portion, and
   (ii) a flexible distal portion;
(c) a deflection actuation assembly comprising:
   (i) a first rotary actuator,
   (ii) a first translatable actuation member operatively coupled with the first rotary actuator, and
   (iii) a second translatable actuation member extending through the shaft assembly, wherein the second translatable actuation member couples the first translatable actuation member with the flexible distal portion of the shaft assembly, wherein the first rotary actuator is rotatable about a first axis to thereby drive the first and second translatable actuation members longitudinally, wherein the flexible distal portion is configured to deflect away from the longitudinal axis in response to translation of the first and second translatable actuation members longitudinally;
(d) a shaft rotation assembly, wherein the shaft rotation assembly is operable to rotate the shaft assembly about the longitudinal axis, wherein the shaft rotation assembly includes a second rotary actuator that is rotatable about a second axis, wherein the second axis is perpendicular to the first axis; and
(e) a dilation catheter, wherein the dilation catheter is slidable relative to the shaft assembly, wherein the dilation catheter comprises an expandable dilator.

2. The apparatus of claim 1, wherein the deflection actuation assembly further comprises a cam follower fixedly secured to the first rotary actuator, wherein the first translatable actuation member comprises a cam channel, wherein the cam follower is disposed in the cam channel.

3. The apparatus of claim 2, wherein the cam channel has a helical configuration.

4. The apparatus of claim 2, wherein the cam channel has a plurality of channel portions, wherein the channel portions are in communication with each other, wherein the cam channel further includes detent features providing transitions between the channel portions.

5. The apparatus of claim 4, wherein the detent features of the cam channel are positioned at locations corresponding to predetermined deflection angles of the flexible distal portion of the shaft assembly.

6. The apparatus of claim 1, wherein the first translatable actuation member is coaxially and slidably disposed about a proximal end of the rigid proximal portion of the shaft assembly.

7. The apparatus of claim 6, wherein the first translatable actuation member and the rigid proximal portion of the shaft assembly comprise complementary features permitting the translatable actuation member to slide along the rigid proximal portion while preventing the translatable actuation member from rotating about the rigid proximal portion.

8. The apparatus of claim 1, wherein the dilation catheter further comprises:
(i) a shaft having an outer diameter, and
(ii) a bulbous tip feature, wherein the bulbous tip feature is located distal to the expandable dilator, wherein the bulbous tip feature has a width greater than the outer diameter of the shaft.

9. The apparatus of claim 8, wherein the bulbous tip is deformable to reduce the width of the bulbous tip feature in response to inwardly directed forces exerted on the bulbous tip feature.

10. The apparatus of claim 1, further comprising a guidewire, wherein the guidewire is slidably disposed in the dilation catheter.

11. The apparatus of claim 10, further comprising a guidewire actuation assembly, wherein the guidewire actuation assembly is operable to translate the guidewire relative to the body, wherein the guidewire actuation assembly is further operable to rotate the guidewire about the longitudinal axis.

12. The apparatus of claim 11, wherein the guidewire actuation assembly comprises a collet assembly, wherein the collet assembly is operable to selectively secure a longitudinal position of the guidewire relative to the guidewire actuation assembly.

13. The apparatus of claim 1, wherein the body comprises a body portion and a grip portion, wherein the grip portion is selectively removable from the body portion.

14. The apparatus of claim 13, wherein the body portion and the grip portion include complementary rail and recess features that are configured to provide sliding longitudinal engagement between the body portion and the grip portion, wherein the body portion and the grip portion further include complementary detent features that are configured to selectively maintain a longitudinal position of the grip portion relative to the body portion.

15. The apparatus of claim 1, wherein the second translatable actuation member comprises a pull-wire.

16. The apparatus of claim 15, wherein the first translatable actuation member comprises a cam barrel, wherein a proximal end of the pull-wire is secured to the cam barrel, wherein a distal end of the pull-wire is secured to a distal end of the flexible distal portion.

17. The apparatus of claim 1, wherein the first axis is coextensive with the longitudinal axis.

18. The apparatus of claim 1, wherein the second axis is perpendicular to the longitudinal axis.

19. An apparatus comprising:
(a) a body;
(b) a shaft assembly extending distally from the body, wherein the shaft assembly defines a longitudinal axis;
(c) a dilation catheter, wherein the dilation catheter is slidable relative to the shaft assembly, wherein the dilation catheter comprises an expandable dilator;
(d) a guidewire, wherein the guidewire is slidable relative to the shaft assembly; and
(e) a shaft rotation actuator, wherein the shaft rotation actuator is rotatable about an axis of rotation that is perpendicular to the longitudinal axis of the shaft assembly, wherein the shaft rotation actuator is operable to rotate the shaft assembly about the longitudinal axis of the shaft assembly in response to rotation of the shaft rotation actuator about the axis of rotation that is perpendicular to the longitudinal axis of the shaft assembly.

20. An apparatus, comprising:
(a) a body;
(b) a shaft assembly extending distally from the body and defining a longitudinal axis, wherein the shaft assembly comprises:
   (i) a rigid proximal portion, and
   (ii) a flexible distal portion;

(c) a dilation catheter, wherein the dilation catheter is slidable relative to the shaft assembly, wherein the dilation catheter comprises an expandable dilator;

(d) a deflection actuator, wherein the deflection actuator is rotatable about a first axis, wherein the flexible distal portion of the shaft assembly is configured to deflect away from the longitudinal axis in response to a rotation of the deflection actuator;

(e) a shaft rotation actuator, wherein the shaft rotation actuator is rotatable about a second axis, wherein the shaft assembly is configured to rotate about the second axis in response to a rotation of the shaft rotation actuator, wherein the second axis is perpendicular to the first axis;

a guidewire, wherein the guidewire is slidably disposed in the dilation catheter; and (g) a guidewire actuation assembly, wherein the guidewire actuation assembly is operable to translate the guidewire relative to the body, wherein the guidewire actuation assembly is further operable to rotate the guidewire about the longitudinal axis.

\* \* \* \* \*